(12) United States Patent
Jiang et al.

(10) Patent No.: US 7,662,567 B2
(45) Date of Patent: Feb. 16, 2010

(54) POLYMORPHISMS IN THE UROCORTIN 3 GENE AND THEIR ASSOCIATIONS WITH MARBLING AND SUBCUTANEOUS FAT DEPTH IN BEEF CATTLE

(75) Inventors: Zhihua Jiang, Pullman, WA (US); Jennifer J. Michal, Albion, WA (US); Galen A. Williams, Beaverton, OR (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 11/985,453

(22) Filed: Nov. 15, 2007

(65) Prior Publication Data
US 2008/0171336 A1    Jul. 17, 2008

Related U.S. Application Data

(60) Provisional application No. 60/859,352, filed on Nov. 15, 2006, provisional application No. 60/859,353, filed on Nov. 15, 2006.

(51) Int. Cl.
*C12Q 1/68* (2006.01)
*C12P 19/34* (2006.01)
*C07H 21/02* (2006.01)

(52) U.S. Cl. .......................... 435/6; 435/91.2; 536/23.1

(58) Field of Classification Search ....................... None
See application file for complete search history.

(56) References Cited

OTHER PUBLICATIONS

Thisted R.A. 'What is a P-value?' (May 25, 1998) from www.stat.uchicago.edu/~thisted, pp. 1-6.*

Michal J.J. et al. 'Association Of Urocortin 3 And Corticotrophin-Releasing Hormone Receptor 2 With Subcutaneous Fat Deposition And Marbling Score In Wagyu X Limousin F2 Cattle' Abstract P526 from Plant & Animal Genomes XV Conference, Jan. 13-17, 2007, 1 printed page.*

Juppner H. Bone (Aug. 1995) vol. 17 No. 2, Supplement, pp. 39S-42S.*

Hacker U.T. et al. Gut (1997) vol. 40, pp. 623-627.*

Jiang Z. et al. 'Cross Species Association Examination of UCN3 and CRHR2 as Potential Pharmacological Targets for Antiobesity Drugs' PLoS One (Dec. 2006; issue 1) 1(1): e80, 8 printed pages.*

Tsuji et al. An association study using AFLP markers and application to a beef cattle breeding population. Animal Genetics. Feb. 2004, vol. 35, No. 1, pp. 40-43.

Database DWPI on West, Derwent Acc. No. 2002-737829, Abstract of KR 415080 B (Yeo, J.S.) Jan. 13, 2004.

* cited by examiner

*Primary Examiner*—Stephen Kapushoc
(74) *Attorney, Agent, or Firm*—Judy Jarecki-Black; Merial Limited; Thomas Kowalski, Esq.

(57) ABSTRACT

Aspects of the present invention also provide methods based on novel UCN3 nucleotide polymorphisms selected from the group consisting of AAFC03043460.1:g.8272-8281AATAATAAAT(SEQ ID NO: 9)>GGAGC, g.8208C>T, g.8265C>T, g.8287T>C, g.8412A>G, g.8426T>A, c.8786C>T, g.9074T>C, c.12609C>T, c.12621T>C, c.12667T>G and c.12669C>A, which may provide novel markers for marbling and/or subcutaneous fat. Additional aspects provide for novel methods which may comprise marker-assisted selection or marker-assisted management to improve marbling and/or subcutaneous fat depth in cattle.

1 Claim, 13 Drawing Sheets

FIG. 2

Bovine UCN3 genomic DNA sequence.
>gi|112135004|gb|AAFC03043460.1| Bos taurus Ctg89.CH240-325G3, whole genome shotgun sequence CTTCATCTGAGATTTAGAGAGAGAAACGTTAGAGACTGAACAAGCCAGCAACATTCCCCAGAGAAATGGTGAACT
TATTTCCCAGTGGAGATAGATGCGTCCTGTTCATCCTCACCTCTTATACTAAGTGTAAATTTTGATGTCTGAGTC
TTTTGGTGGCCCCCAAGATTGGACTTGGATGTCCTTAATGTACCCTGGTCTTTCCCTCTTATAGTAATGGGTCAT
CCCACTGTCCAGCCACTTCCCTCTTTATCCATCTTCAGCTTACTCCAGCCCACCTGGCAGGTGCTTCAGATTCAA
GAGACCTTAATTTGCATTCTGATATATTGCTATTAAGACTGAAAACTGCTACTTATTGTTATAGAGGACAATTGG
CAATATTTGTCTAATCTTATCATATCTTTTGGGCTTCCCTGGTGGCTTTAAAAATTATAAAAGAACAGTCTTTGA
TCTGGCAGTTCTTACACATTTAACCAAACACTTAATCTTCCAAGTGAAGGATGAACAGGAATGATCCTCTCTCAA
CAGGAAATGAGTTCATCATTTGTTCTGAAAGATGCTGCTTTGAAGGCAAGAATCATGACTATCCTGCTCCATCTT
CAATTTTCAGAAGTCAAGACTGTCCCTAACACCCATAGGCATTCAATAAATATTTAAGTGAACAATTGACCTTAC
CAAAAATTCAAATTGCCTTCATCATGTAAAACCTATTTTTATAAACTCAGTTTGCTCCTCTTCCAAACGGGACAG
TTAACTAGTCCTATTGTTTTGAAAGGGCAAAACAGGGTGTCTCTGAAGCTCTTCCTGAGTTGAAAACTGAAACAT
TTATTACTGACATTTAAGTGTTGCTCCCACCTACTCCCCTTTGCAAATATTTCTGAAGAAAATTCATTTCCAGA
TAGATATATCCTCATTTACATCTAATTCTCTGCATATTACTCAGTGGAGGAGGGCCAGCAAAGGTTAGGGCATCG
GAGAAAGGTGACAACCAGAGACTCGAGTGAATGCAGAGCTTTAATTGGCAATTAGTCAGAATGAAGTAAGAGATG
GTGGAACTGGGTGCCTGTTCTAGTACGCAGCAAAGAACTCTGCATTGTGACCGCATTACAAAGAACACGGAAGAT
ATCTTTCCATTTTATCTAAGTCAATGTACTTAAGGGCAGAGAGGTGTTTGTCACAGTCATTACTGTCCTGAAGGG
TCAATAATGAAGTTCCTCTTGGATTCCTGATATCAGTAATTTGGGTCTTCTCTCTTTTATTCATGGTCTAGCTAG
AGGTTTATAAATTCTGTTGCTCTTCAAAAAATACCAGCTTTTGTTTTCATTGTTCCTCTCATTTTCTAGTCTCTA
TTTCATATATATATGTATATATACACAATGATGTATATCACACTGCATGTGTGTATATATATATATATATATATC
TCTACTCTAAGATATATATATATACTCTGAAGCTGAAACTCCAATACTTTGGCCACCTGATGTGAAGAACTGACT
CATTGGAAAAGACCCTGATGTTGGAAAAGATTGAAGGCAGGAGAAGGGGGTGACAGAGAATGAGAGGGTTGGATG
GCATCACCAACTTGATGAACATGAGTTTGAGCAAGGTCCGGGAGTTGGTGATGGACAGGGAAGCCTGGCGTGCTG
CAGTCCCTGGGGTCACAAAGAGTTGGACATGATGGAGTGACTGAACGGAACTGACTCTTATCTTTACTACTTAAA
TTCCTTGCTTTGGACTTAACTCGTTTTTCTTTTCTACGTGAAAGCTTAGATCACTGGTTTGAGACCTCTCTTCT
CTTCCCATATAAGCATTTAAAACTATAAATTTCCTCTGTATGCTGCTTTGAATACATGCCACAATTCTTAATATA
TTGAAGGAGCAATTCAAATTTCAAGGGGTATGCAAGTCAAGCTGTGTTCCTCGAAGATTTAAAAAGCTGATCATT
TCCTCATACAACACCCCCCACACACACACACACACATACACAATCACAATGTTGATATTTGGTTAATTTAGATAA
GGAGTATACCTTTGTTCATCACACTCATTTCTACTTTCCTGGAAACTTTCTGAAAAACAATTGGAGTTTTAAAAG
AGTGCACAGAAAGTTATTGGGCAACTGCCTTGTTTTACAGGGCTTCCCAGGCTAATGCAGGAGACATAGGTTCA
TCCCTGGGTCCAGAAGATCCTATGGAGGAGGAAATGGCAACCCACTCCGGTATTCTTGCCTACAAAATTTCAAGA
ACAGAGAAGACTGGCAGGCTACAGTCCATAGTATCGCAAAGAGTCAGATACGACTGAGCACAAATGCTTGTTTTA
CAAGAGAGACAGTGAGCTTGCAATCATGGTAAGGCACTAAGAAGCTGCCATCTTCAATAACAAGGTTTGGATTGT
TGAAAACAAGCCTAGGAGAGAAGGACCAGCTGGTGGGAATGAACAATGGACTGTCATGAGGGAGGATCTCATTTT
CACCTCTGAGCTGCTGCAGGGAGACTCCAGGGTGTGGTGATGTTTTCATTAGCAGCTCAGGTTCAGCCCAGGCTT
CTCTACCTTCTACACCGCGTAACATCAGTGCTATTTCCTGCAGACCCCAGGACCTCAGCAGGCACCCGCTGCTCA
CCAAGATGACTGTGGAGACATCCCTTCCCACATGGGAACATGAGCAATCCTGAGAGCTGTCCACCGTCCAGAGTG
TGACATGAAGGAACAGATGTCATCAGCCCCAGGACAGAGAGTAGGTGGAAAGCAAGTCTGGGATGAACAGAGAGA
AATGCAGATTTTTAAATGTTCACAAAGGCAGGGAGAGAGGAAGAAAGGGTAGAATATAAAATAACACCTACGCTA
TGGCTACAAATTCATGCACCCATGTTTTCTCAGATTACCAGTTCAGTTTCTCATGCCTTGGTCTGATGACGTGGG
ACCTGCAGTCCACACCGCCTCCAAGGCCCAACAAGCGATTTCTGGGCCTGTCTTACTGAACAATACTTTTAATTT
CATCCACTTTTGGCCCCTCACCATGGTAAAAAGGTGTCCTTCCCAAAGTTACAGGCCCTGGGACCTGTAACTTTC
CAAAGTTATAAGCCCTGGGACCTGTAACTTCCCAAAGTTACAGGCCATGGGACCAAAGTGACACTGGGCTTTCAC
TGGGGAGTAAAGTCAAGCTGGGAGAAGGCAATGGCACCCCACTCCAGTATTCTTGCCTGGAGAATCCCAGGGATG
GGGAAGCCTGGTGGGGTGCCGTCTATGGGTCGCACAGAGTCGGACATGACTGAAGCAACTTAGCAGCAACAGCA
GCAAAGTCAAGCTGTGTTCCACAGAGGATTAAAAAGCTGATCATGTCTGGGCTTCCCCAGTGGCTCAGTGGTAAA
GAATCTGCCTGCCAGTGCAGGAAACCCAGGTTTGATTTCTGGTCCAGGAAGATCCCACATAGCCCCCTAGGAGCC
ACTATGCCCATGCACCACAACTGCTGTGTGCCCTAGAGCCCAGGAGCCGCAACTACTGACCCCACAACCACAACA
GCTGAGCTCCTGCACCTGGAGCTCGTGCCCTGAGACGCACCACAACGCGAAGCCCACACCCCACAACTACAGAGG
AGCCCCCACTCGCCGCAACTAGAGGAAGAGCCTAAGCGGCAACAAAGTCCCAACACAGCCAAAAATAAATAGAAT
TATTTTAAAAACAAATTAAAAGCTTATCATTTCCAATCTTCTTGTGAGGCTCTCTTCCCATTTAACTACCTGATT
CTTCAAACTTGTCTACAAAAATACTCCTGTGATACAGCCTTTGGTTAGCGCTTCCAAAGGCTGTTCTTCTCACCT
GAGGCTCTTATTAAAAGGAAGTTTGATTCATTAGGGCTGAGGTGAGATTCTGCATCTCTAAAAGCTCCCAGGGAT

FIG. 4A

```
GCTGAGGTTGAAGGTCCATGGACCACAGTTTGAGCAGCTGGCTTCTATAGTTCTTAGTACTTACTATAGTCCTTA
GTATTAAATATTAACCACTTGTGTTTCTTGTCCTTAGTAGGTCTACAATAAACCTGACTTGGAGGGATGGCTTTT
TGATTGAAGTATAGTTGATTTACAATGCTGTCTTAGATTCTGATGCTGCTGTTGTTGTTGTTCAGTCACTAAGTC
GTGTTCAACTCTTGGTGACCTATGGACTGCTGCTCACCAGGCTCCTCTGTCCTCCACTACCTCCCGGAGTTTGCT
CAAATTCATGTCGATGATGCTATCCCAACCATCTCATCCTCTTCCACCCCCTACTCCTTTTGCCTTCAATCTTTC
CCAGAATCAAGATCTTTTCCAATGAGTTGACTCTTCACACCAGGGGGCCAAAGTATTAGAGCTTTTAGTTTCTGC
TGTACAGCAAAGTGAATCAGCTATATGTATACATATACCCCTCTTTTTGGATTTCCTTCCCATTTAGGTCACCA
CAGGGCATTGAGGAAAGTTCCCTGTGCTATACAGCAGGTTCTCATTGGTTATCTGTTTTATACACAGTATCAATA
GTGAATATATGTCAATCCCAATCTCCTAATTCATCCCATGGAGCTATGATTGAATTTATTAAATGTTTCTACAGT
AGTAGAATAAAGAGGGAAAGCTTTACCAACACATCAGTCTTTCATCCTACTCATGTTCCCTCTCTTTTCTTGGAG
TTAAGGAAGCCAGGGCATAATTGGGTGGAGGCAGACTTGGCAAAGTGGTGTTTCTTTTCTGGCTTATAGAGCAAA
ACAAGAAAGGCTGGAGGTGGAGTCAGTGGTGGAGGTCTCTGCCCATGTGGCCAGTGATCCAGCACCATGGGATGA
ACCTGCTTTTCCTGTTTGTAGCAGCTCTCCTCCCTAACCTCATGACAATTACTGGCCAAAATTCAGAACTGTCTG
TTTTTTACTCTCCCCCTACTATTTCTGTCTTGTACACCTGTATACAAACAAGTGTACTCCCTGAAATTTGAATTG
TTCCTTCTGCCTCTACAATGGAAACTGTAGGATTTTATACTCTAAAAAGCCAACTATAGTGATGACATCACTGTC
TTCTAACCCAGCCTCATTCTGTGGAGACCTGCACACATATCCTTCACCCTCCCTTGATTATTAGAGATGAAATGG
AATCTCAATGCAATTTGAGTCCCCGTAACTTGTCTTTTTGAATAAACCTCTAATAATCTCTTTTTAATTTCATTT
CAATACTATTATCTTCAATTATGGGCTCCGTGTCTACAACAATCCCTCACTCTCAAGGCCAAGTTCTGTTCTCTC
CTTGTAGTTGGAAATGCAGGCTTATCCAGCTTTGCAAAAGAGATCATCCTTGAGAATGTTCATGTCGGGGCCTG
AGTTCTGAGGTTCACCTGTGTGTGACCCCAGCTAAGAGACTGAACTAGAGCATGAACTCTCTTTTAGGCCAAACA
TTCTGTGATTCTGTAAGAGTTCATGCAAACAAAAGCATTTAAAATACTAAAGAATGTCTGTTGGGACTTCCCTGC
TGGTCCAGTGGCTAAGACTCCACGCTCCCAATGCAGGGGCCCAGGTTCTATCCCTGGTCAGGGAACTAGATCCC
ACATGCCACAGCTAAGACTCAATGCAGCTAAATAAATTTTTTTAATATATATTATCTGTTTGGATATATGTGAC
GGGTTGCAATTGTATATGCACATATACGGAGCTACTGAATAAGGAGGATCAACCTCACTTGTTGAGTCTCTGCTA
AACAGCAGATGCTGTGTTCATGGTGCTTTTCCTGGCATAGACTTCAGTCTCAAGCTGCTTACAGACAAACGGACA
CAGTCAGGAGAAGACCACAGCCAGTCTCAAAGCCTAGACTTGCCAAGGGAAACAGATTAAAATTCACAGTAGATA
GGAACATGGTGGTTTATTTCTGATTGATTGATTGATTGGTGAACTGATTAAGCATAGTCCCTGATTAGCTGGCAG
GCATACTTTGGCCACATGATGCGAAGAGTTGACTCATTAGAAAAGACCCCAATGCAAGAAAGATTGAAGGCAGGA
GGAGAAGGGGATGACAGAGCATGACCAACTCGATGGACATGAGTTTGAGCAAGCTTCAGGAGCTGGTGATGGACA
GGGAAGCCTGGTGTGCTGCAGTCCATGGGGTCGCAAAGAGTCAGACATGACTGAACTGAACTGAATAATAACATA
GTGTGCTATGTGTTGGGCTTCCCCTCGATGGCTCAGCAGTAAAGTATCTGCCAGCAATGCAGGAGATGTAAGAGA
TGTGGGTTCAATCCCTGGGTCAGGAAAAGCTCCTGGAGGAGGCCATGGCAACTCACTCCAGTATTCCTGCCTGGA
AAAGTCCATGGACAGAGAAGCCTGGTGGGCTACAGTCCACAGGGCTGCAAAGAGTGGGACATGACCGAGCAACTG
AACAACATATAGATAAGAGATTCTGAAACATGTTCAGGGGTGGGGTGGCAGAGTGCGTGTATTAGCCTTGGAAG
AACGTGGGCTGCTTGGTTACCATTACTACTTACTTTTCCCATGAGCAGAACCACAAGTGAGCTCACCATCCTGGC
CCCATCTGGGAGCATGCTGCCCAGTCCACTGCTTTGTAAGATGTTCGGAAGAGTTTCCAATTCCCTTGTCAATAG
AGAAAACATGTCCCCTAAGTGTATCTGTTGGTGTTGATCCCCTTGTCTACAGGTCAGGTAAACAGGGCACTGTGA
TTGTGTCCACATGTGGAAAAGTGGCTATGGGGCAGTTTGCAAGTTTGCCCAAGAAGCCAACGTCCTCCCCTTCCC
CTGGAAGGAGACAGAAAGCTTTTTTTTTTTTAAGGTTATTACTTTACTATTTATTTATTTGGCCATGCAACATG
AGGGATCTTAGTTCACTGACCAGGGATCAAACCCACACCCCTGCAAGGGCAGCATGGAGTCTTAACCACTGGAC
CATCAAGGAAGTAAGTCCCAGACAGAAAGCTCTGATGCTGTTTCACGAGGCCCCGAGGGAGGCAGCTGCCTCTAG
CCTGTGGCTCCCAGGAGCTTTGCTCCAGGAATCAATCAGCCACTAAAAGTCCATCAGAGAGGATCATAAAACGTC
TGTAATTCACCATGGCACCTGGACACAGAGACAGGCTGGAACTGTCCCCACCTGTTTCCACCGCTGCTGGTTTCA
AGGGGGATGCAAAGTCCAATGAGATTGATTCCTGATAGGTGGATAGGAGACAGCGCTAGAGAACCCATATCAGAA
AGGACTGGATGTTAATGCAGGATCATGGGTGTGCTGTTATTATAGAAGTACAGTTACTAATAACTAAATCAGTCC
TGCCTGTTGGGAAAAACAAGAGTCAAGGCAAGGGTCTCCCCTTACTTCACAGACCAGAGAAATTTCACCAGGTTA
CAGGGGGCTCTGTTCATGTGTGAGGTGTAGTGAATCAGTGCTCAGAGCAAGAACTGTAGTTTTTGCATGCTCATT
TGCTCAGTGGTGTCCGACACTGTGTGACCCCATGGACTGTAGCCCACCAGACTCCTCTGTCCTTGGGATTCTCCA
GGCAAGAATACTGGAGAGGGCTGCCATTTCCTCCTCCAGGGGATATTCCCAACCCAGGAATCAAACCAGAGTCTC
TTACAGCTCCTGCATTGGCAAGATGGTTCTTTACCACTGAGCCACCAGGGAAGCCCCAATTGTAGTTTTAAATGC
CTAGATACAAACTAATAGCGGGGAAAATGAAATGAAAATTTAATCAATCTAGAAGAACACAGACAAGGAAAAAGA
GAAATAAACAGAAACAGAGGGGGAAAGCAGACCAAATAGGAAATGTTTTACATGTGAAACAGCAGAAATAATCC
GAAAACATCAGTAATCATTATTCATACAAATGTGTCACGTCAGTGATCACTATTAGTACAAACTAATACAAAGGC
CTGTATTAAGGCCTTGTTAATACAGAGATGGTTGATTAGATTTTTTAATTTCAGTATATACCCTTCACAAAAGAA
CTTTGACACAAAAAAACTGGAAAAAATGCACCAAGCAAATGTCAACCAAAGGAAACTGGAATAGCTGTTTCAGT
ATCAGACAAAGCAGACTGTAAGACAAAAAGTGTTATTTGATTTGAAAGGGTTTATAGTCAAATTATTAAAGGGGT
```

FIG. 4B

```
TATTTGCATTGAGCTGGCCAAAAAGTTCATTTGGAATGTAGCTAGGCTGTTCAATAAAGGTCTTGGTGAAAATGC
AAACTGTGCCTAAGCCCACACACTGCAGCTACCGAGCCCATGTACCGCAACTGGAGAAACCTGCACACTGCAATG
AAGACCCAGAACAGCCAAAATAATAATAAATAAGTGTTTCCATTGCTCAGTAGCTAAGTCGTGTCTGACTCTTTT
TTGACCCCATGGACTGCAGCACGCCAGGCTTCCCTGTCCTTCATAACCTCCAGGAGTTTGCTCAAACACTTGTCC
ATTGAGTTGGTAATGCCAAAGAAATTAAAAAAAAAAAAAAAAAAACTAATCACAGGACAGCAGACAAACTTTCTT
CTCTACTTTCAAGCAGGTGTTGGCTCCAGGAAGAAGGGTAGAGAGACTGAAATTAGTAAGAACGAAGATGAGTAA
TAAAACTCTTCAAAGAAGCTGCTTCTCAGTTTAACAGAGTGTGTTTTTTCCTTTTTATCAATGAAGCCAGTTGCT
AGGGCAGGAAGGGCAGTGGGGGGTGGGGCGGTGATGGGAGGTCTGGGAGAGAAGGTGGGTAGGAGCGGTCAGAG
ATGCTGACAGCTTGTCATCTCCGTGACGTGCACAGCTGCTTGGGTTGTATTTTAAACGGGATCACATCCCAGGGT
AGACACCGTGTCTGGATTTATGATCCACCCGTGATCTGTCACTTTTATGTATATGCACACACACGAGGGAGTGG
AGTGGTTTCCATAGAGAGGAAAGATCACGGCCCACTTACAAACGGCCCACTTACAAACAATTCAAGAAAAGGAGC
CGGCGACCCCAGAGAAGACAGAAGTTCGGGGGGATGTTCCTGGGGCAGACCTCTCGGTTCTGAAGCTGCCCGCC
CGCCTCACTGAGCATTTGCACTCCAGAGTGAAGTCTGCTCACAGGTAAGGCTCTGGTTGGGGACTTCCCTATGAA
GGATCACTTGATTTGCCCTTAATTATGCAGGAGGTGCTGGGGACTGGATGGGGTGAGCGATAAGAGTTGCAAGCA
CCCCTGGGGGCACTGTGCTGAACCGTCAATGTCTGTGTTTTAAATGGGGAGAAGGCAGACCCAAAGGGACCAAGG
GGAAGTTTCTCAGGGGGGGCAAGAGCATCCTCCCCCCATTAGTAGAGAGGCCTGCTTTGCAAAAGGTAATAGACC
GGAAGCAGGATGGGTTCTCACAAACGTGTTTTTCTGAACAGAGTCCAGTTGTGAACATGAAAATCGTGTTTCCAG
ATGGGGTGGATGGGGAAGATGGGGGTGGAAACCGGGGTACCAGTCCCTGCTGCCTGACCGATCGGGAAAATGCTT
GCATTTCCTGGTTGCTAAGGCATCTCCTTTCGTTCTCTTCATACACCTGTGAGGCAGGTAACGCCTGCTTTTTAA
GATGCGGTGACTGAGAGGTTAAGTGACTGATGGAAGGCATTTGAGGGTGAGGGAGGTTCGCAGCCCAGGTCCTCT
GCCCTCACAGCCTGGAGTCCTTTCCCCCTGGCCACCAGGGACACTGGAGGAAGGGAACAGATGTCTGTAACAATT
AGGTGCCCCCCCTTGAAGGGGAGAGGCCATAAAGATGGATGTTTGATGTCTCCATTTGATGTCCAAGTGTTCTGA
GAAATCCTGTCTGCAGGGTTCTCCTGTAACACAGCAATCTAGCCAGCATTCCCACTTCTGAGGATGAATGGAGTC
AGAAAAGCAACACAAAAGCTTCCAGTAACAAGTGTTATCTAGATCTTGTCAACTTTCTCCTGGCTTTTCTCCCTC
TTGGGGGGAAAGGCCTTTCATGAATGAACCCCCTCTGCTCGCTCAAGTGTGAATTGCTAAGAAGTGTGTGTGTTA
CACATAAATGCTTCCATGAGTCTGCAGCTCATTACTATAATATCTTTCAAAATGCTTAAAGGGTCCCTGGGTTCA
GCAGTGACTGTTTTATAAAGTGTTTTTTTAATTCAACTTCTTACCCGTGATTGCAGACTGCGAACTATCTCTGCC
TTCCTAGATGCTGGAAAATGGGGCTGCCTCTGGGCAAAGCCCGTGGTGTCCTGCATTTGCCTCTAGCTTCACTTT
TTTCCTTCAGGGAGCTGTCTCTCACAGGTGCTCTGAATTTCAGACCAGCTGAGTCCCTCGCTGCCTGTCATTCTG
GGCACGACGTGACTGTCACAGCTCTTAGAAGCAAGTGTCCGTCTCCAGAGAAGCACTGCCCTAATAACCCCCAAA
GAATGGCTGAGTGTCAGGTACCCAAATGAGAAAAATGAAGATGAAGAACGTTTCCCTGTAAACCTAACTAGATGG
GGGCCACGTGTTTTCAGAGCAGGTAGCAGGGAAATCTTAAACCTTTGTACTCTTGCACTATGGTAAAGGCAAAGG
AATCCAAAGAATGTAAGAGGAGAAACTTGCTTAGGAATCAGACCTGAGTAAGGAGGAAAGGACGTTTCTTTTCTT
TGACAGTCCTCTCTGTTCCTGGGATTGGCTCCAGGACCGTCACAGATCCCCAGATGCTCAAGTCCCTTATATAAA
ATAATGTATTATTTGCACATAATCTACAAACATCCTCCCATGCAGGGGTGAGTGCTAAGTCGCTTCAGTCGTGTC
CAATCCTTTGCAACCCTATGGACTATAGCCCGCCAGGCTCCTCTGTCCATGGGATTCTCCAGGCATGAATACTGG
AGTGGGTTGCCATGTCCTTCTCCAGGAGATCTTCCCCGTCTTAGGGATTGAACCTGTGTCTCCTGTATTGGCAGG
CAGATTCTTTACCACTAGTGCCACCTGGAAAGCCCCACAATCTCCCATGGTTTTATGCAAATGCTAAACAAAGCT
AAACTGGAGAGAGAGGGAGAAAAGGAGAGAGAGAGGAGAGCCTGGAGCTCAATCCCCTAATCTCACAGATGGGAA
CACAGGGACCAGGGGCATTTAGTCACTGAGCCAGTTAGTGGGAGGTAGGGCCGAGCCTGACCCCTGAAAAGAGCA
GGGGACCAAGGGAGAGAGAGATAGCGACAGAAAGAGACAGATCCCCTCCCACCCCGACCCCCACCCCGTTATTAA
CCCTTTCTCTGTGTATTGGTTTTTGGTTTTTTAATCTTTTCAGGCTTATCAGGCCCTTTGAGAGTGCTCCCAAG
CTTTAAAATGCCTTCAAGGCATAAGGCAGCTAAAGCCACAATTCATGGATGTTTATGCAAAACAACTAAGGACAG
CCTCAATGAATGAGGAAACCAGAAGTCTGGGTATTGAGCACAATATCAAAAGAAAGGATAAGTCCATTCTTCCAC
AGTCTAAAGAGCCCTGTAAAATGTTCTCCGGGAATCGGGCACACAGTTCTAAGGACCTCGGAGATGGATAGGAAC
GCTGAGAAAGTGGTTCACAAAGCGTGGTCCATGAACCCACAGCATCAGCATCCTCTAGGGATGTGTTAGGGATGC
AGATTCTCAGGCCTTGCCCCAAATCTACTGATTCAGAAATGCTGGAGATGGGGCCCAGCAGCTGGTGTTTGAACA
GTTCATTCACGTGATTCTGAACACTCTGAAGCGTGAGAACTGCTGACTTAGAGTTCAAGGCACGATGAGCCTACC
TGGGTAAGAGTGGAGCAAACAGACGAAAAAAGAAAAAGCCAAAAAGCAACACAACAAAGATAATGGTCTGCAGGA
TGAAGTTCCCTGGCATACTATACATCTATATTTATATTCGTATGAATTATATTCATTAGTTATATAATGTATAGT
ACATTTACAGATACACAGATACAGATAGATCACTTCTGAGATGGTTGCCTGTGTACTGAATCTTATCCTAATAGC
ACGTGGGGATTATTACATGTAAACAGTCAGTAACCAACACGCTTCGTTAAGTATTTGGTTAGACAGGGAGCTTTT
CCACTTTAATTTAACCTTTACGAGTTAGTACCTATTATCCCCCATTATTATTATTATCATTATTATTATCAGATG
AGGAAATTGATGTTCTCAGAGGTTAAGTAATCTGCCTGCCACCCTCAAGCAAACAAGGACCCAGTTGGAATTTGA
ACCTACCTCTGTCTAACTCCAGAGCCTGTGTTTCTTTCCATGTGCTAGGTAGCTAGTTCCTACATCTGGACCATT
CCTACATCTGGCAACAGTCTGTCATCATCAGGCTTGTTAACACGCAGATTGCTGGCCCCAGAGCTCTTGACTGAC
```

FIG. 4C

```
CAGCTCTGGAGCAAGACCCGAGAATCTCTGCATTGCTAACAAATGTCCATGATACACGGCCTGCAAGTCCAGAGA
ACACGCTTTCAAAACCCGGCAAAGCTGAACTTGCACAAAGCCTGGTAGATCTGCCCCTTCTCCCCCTGAACCCTA
AGACCCTCTCACACATATCGGTCTTTTCCGCTGCAGGGAGAGATGCTCGTGCCGGCCCCCTTCCTGCTGGTCTTG
CTACTGCTCCTCGGGGCCCCCCAGGTGGGCCTCTCCCAGAGGTCCCCAAAAGCCGGGTCCAGCCCCAGCTGCCTC
CACACAGCCCTACGTGAGGCTGAGAAGAGCCAGCGGAAGGACACGTCGCTGCTGATCAAGCGGACCTTCCCTGCC
CTGCCCCGCGGAGACCCGGAGGACCAGGAGGGGCAGGAGGAGGAGGACACAGAGAAAAGGACCTTCCCTGGCTCC
GTGGGCGGCGGCGGTGGCGGCGGGCCGGCAGCACCCGGTACAAGTACCCATCCCAGGCACAGTTCCAGGGGCGG
CCGTCCCAGGACAAGGCCAATAGTGACCGGCGCACCAAGGTCACTCTGTCCCTGGACGTCCCCACTAACATTATG
AACATCCTCTTCAACATCGCCAAGGCCAAGAACCTGCGAGCCAAGGCCGCCGCCAACGCCCACCTCATGCCCAG
ATTGGGCGGAAGAAGTAGAGGAGGAGGCTGGGGACCCCCTAGGACGAGGACGGAGGTTGGGGGGTGGACAGGGAG
GGTTGGCCCGTCCTGCCAGTTTCTATCGGAGGGATCGGCCCTGGTTTCCAGGCTCTCCACCCCTCTGTGCCTTCC
CGCCTCCAGCTGGGCCCCCCACCCTCTATATCTACACACACCAGCGGCCTGTTGTCCCAGATCCACAGATGGAGG
CCACCGTACTGAGACACTGAGATCTACCCTAGGCGTCTCCTTTCTCCCTCCCCACAAGGAGAGGCAAAGGTCAGG
CACCCCTGCCCTCCACTCCGCTCTCTGACCCCAAGAAGAGGGGTACAGGGAGGCCCTCCCCTCCCCACACCAACC
CCAGCCCAGGCAGGAAGGCGAGGGCGCTGAGCACCCTGCCCCCAGACCCTCATTAAAACCCCTCTCACCCACATT
AAAACCCATGGCTTCTTGAACCCCTGACTGGTTTCAATTCCTCTTCCTTCAGTCAGCTGCCTTCAGGCCTCCAAG
CTTGGAAAGGGGCAGCTAGTGAGACAGGGTACAGGTGAGTCCGTTCCTGACCCTCCCAGGACAGTCCCTGGAGGT
CTTGGGAGGCATCAAGAGCTTGGGAAAGGCCAAGCTGGCAGGACCCTGTTGGCTATCACTGGATCTGAAGCTGGC
TATGTGGCCAGGTCCCACCAGAGGCATAGCCTTGGGTCTGCTACAGAGTGGGCCCCTGGGTAGAACGAAAGACAC
CCCCAGCTCCTCCCTGGCTTGCTAGGGCCTGAGCCACTAAGTCTGTCATAGGTGCTTCTTGAATCGATGGTCATT
GTCCAGCCCAGTGCTGGGCCTAGTTAGGGATACTGACGTGGGAGGCGCCAAGGCCCTTGCTATCCATGAGTCAAC
AGTCTTAAGTGAACAGACAAAAACAAAATGTGAAAAGAAGCAATTTCACTAGGGAGTATATAAGTGATGAACTGC
AAGGTCATAGCAATTAGTGTAAAAAATACAAGGAAATCAGAGCAAGATGAGAAGGCTTAATATGAGAAGCAGTTC
ACTAAAAATGGACATCAGCAAGCACCCTGATGGCCTCTGGCAGCAGAGCTTTCTGCATGGTGACAAGTCATGAAT
ACATACAAAGAACATCTTCACGTGAAATAAACCTCATATGCACACACCACCACCATCAGACAAAGTCAAGAGACA
AACAGACAACAAATTTGGAAAAATGTTTGCCACACAGGCAAAAGACAAGTATCTTACTGATCAAATACGTAAAGA
GCTAATAACTTCCCAGGTGACACTACTGGTAAAGAACCTGCCTGCCATTGCAGGAGACATTCGATCCCTGGGTTG
GGAAGATCCCCTGGAGGAGGGCATGGCAACCCACTCCAGTGTTCTTGCCTGGAGAATCCCATGGAGAGAGGAGCC
TGGCGGGCTACAGTCCATAGGGTTGCAAAGAGTCGGACATGACTGGAGCAACTTAACACACACAAACACGCACAC
AAAATAACTGAAAAAAAAAAACAATCGCCCTCAAAAAAATAAGCAGGAATACATATATCACACACACACAAATAC
AAGTGACCCTTAAATGTACAAACAGATGCTAAACTTCACTGCTAAAAAAAGCACAACTGCACTCTTACAGAATTT
GTCACACATCAGACTGGCAAAATCTGTTTGACAATCGGTTCACACTGTGACTGACAGGTGCAAAGCCTCCTTCCT
TCACTGATGGTTGGTGGGAACATGAATTCTGAGAGGCAATCTGGAAAATCCGTATCAAAACCACAAATTCACTTT
ACCTTTAACTCAACAACCCTGATTCTGGTGAACATTATTTGAAAAGGCAAAACTGTGCAGTTTTTTAAATGTTAA
GCTAACTTGGAAATGAAAAATACCCCATCTCTAAACAGAACCAATGCTCAAAAAGCTGAAATGCAGCTGTTTTTT
CCATCCTGGGTGGGGGGAAAAAACCCTCATGACACAGCAGAAATACCTATGTGAGTCCGGGTTCCTCCTCTTCTG
TGTCTCTGAGCAAATCCTTTAACTTCCCTCAGCGTTGGTGTGCCAGGAACCCTCTTTAGGAACGAGACGTCACGG
AGTTCTCACAAGTATATTTAACATTTATTTTTGTTCTAACAGTGCGTGCAGCATTCTGCTCACACCAAAGATGCA
AAGGACAGGAAATTGGCGGGGGGGTGGGGGGGGTGGGAATTAGCTTGGTTAAAGAAAACTCAAGCAGGTATGAC
ATTTCCCTGAACAACCAAAAACACTAGAAGAACTTCCAAGTTGGGGAAATGGTACCTGCAAGCACACCCAAGTTC
ACAGCTATCTCCTCTTAGGGCCTTTGGCTAGGTGAACAAAGCCTTGAAGACAGCAGCCT
```

FIG. 4D

POLYMORPHISMS IN THE UROCORTIN 3 GENE AND THEIR ASSOCIATIONS WITH MARBLING AND SUBCUTANEOUS FAT DEPTH IN BEEF CATTLE

INCORPORATION BY REFERENCE

This application claims benefit of U.S. provisional patent application Ser. Nos. 60/859,352 filed Nov. 15, 2006 and 60/859,353 filed Nov. 15, 2006.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

Aspects of the present invention relate generally to obesity and to obesity phenotypes, and more particularly to novel genetic markers and determinants (e.g., urocortin 3) of extreme obesity phenotypes (e.g., regulation of both muscle fat deposition and subcutaneous fat deposition). The invention further relates to methods and systems, including network-based processes, to manage the MNP and SNP data and other data relating to specific animals and herds of animals, veterinarian care, diagnostic and quality control data and management of livestock which, based on genotyping, have predictable meat quality traits, husbandry conditions, animal welfare, food safety information, audit of existing processes and data from field locations.

BACKGROUND OF THE INVENTION

Obesity has increased at a fast rate in recent years and is now a worldwide public health problem. The major consequence of overweight and obesity is that they are associated with more than 30 medical conditions, which cause approximately 300,000 deaths and total medical expenditures (direct and indirect) of $139 billion annually in the USA alone (Finkelstein E A, Ruhm C J, Kosa K M (2005) Economic Causes and Consequences of Obesity. Annu Rev Public Health 26: 14.1-14.19). Insulin resistance, a characteristic of obesity, prevents insulin from taking the sugar from food and distributing it throughout the body for energy. Many studies have clearly indicated that intramyocellular accumulation of triglycerides is a major contributor to insulin resistance (Goodpaster B H, Wolf D (2004) Skeletal muscle lipid accumulation in obesity, insulin resistance, and type 2 diabetes. Pediatr Diabetes 5: 219-226).

Therefore, identification of genes associated with intramyocellular lipid accumulation would provide a clear target for pharmaceutical intervention and care for obesity and its related conditions, such as high blood pressure, type 2 diabetes, coronary heart disease, some types of cancer, poor female reproductive health and psychological disorders.

Urocortin 3 (UCN3) is a member of the corticotropin-releasing hormone (CRH) family of peptides. UCN3 binds selectively to CRHR2 (Lewis K, Li C, Perrin M H, Blount A, Kunitake K et al. (2001) Identification of urocortin III, an additional member of the corticotropin-releasing factor (CRF) family with high affinity for the CRF2 receptor. Proc Natl Acad Sci USA 98: 7570-7575) and both are co-expressed throughout the central nervous system, such as in the ventromedial hypothalamic nucleus, lateral septum and bed nucleus of the stria terminalis (Li C, Vaughan J, Sawchenko P E, Vale W W (2002) Urocortin III-immunoreactive projections in rat brain: partial overlap with sites of type 2 corticotrophin-releasing factor receptor expression. J Neurosci 22: 991-1001), as well as in the gastrointestinal tract (Zorrilla E P, Tache Y, Koob G F (2003) Nibbling at CRF receptor control of feeding and gastrocolonic motility. Trends Pharmacol Sci 24: 421-427). UCN3 is, therefore, thought to play a central role in appetite and gastrointestinal motor regulation. For example, intracerebroventricular injections of UCN3 were found to reduce appetite by suppressing food intake in the freely-fed rat (Ohata H, Shibasaki T (2004) Effects of urocortin 2 and 3 on motor activity and food intake in rats. Peptides 25: 1703-1709).

On the other hand, there is increasing evidence supporting the involvement of this peptide in the regulation of energy homeostasis and in mediating the anorexic effect of CRH at the adipose level. For example, Seres and colleagues (Seres J, Bornstein S R, Seres P, Willenberg H S, Schulte K M et al. (2004) Corticotropin-releasing hormone system in human adipose tissue. J Clin Endocrinol Metab 89: 965-970) found that UCN3 is expressed in human visceral and subcutaneous adipose tissue. Obviously, the local production of this peptide within the adipose tissue indicates its direct involvements in fat cell function in addition to its central effects on weight regulation. Thus, Applicants hypothesized that genetic polymorphisms of UCN3 are associated with muscle fat deposition and subcutaneous fat depth (SFD) in mammals.

Citation or identification of any document in this application is not an admission that such document is available as prior art to the present invention.

SUMMARY OF THE INVENTION

The present invention relates to the identification of genetic markers (multiple nucleotide polymorphism (MNPs) and single nucleotide polymorphisms (SNPs)) within the bovine gene encoding urocortin 3 (UCN3) and their associations with economically relevant traits in beef cattle production.

The invention encompasses a method for sub-grouping animals according to genotype wherein the animals of each sub-group have similar polymorphisms in a UCN3 gene which may comprise determining the genotype of each animal to be sub-grouped by determining the presence of MNPs and/or SNPs in a UCN3 gene, and segregating individual animals into sub-groups wherein each animal in a sub-group has similar polymorphisms in a UCN3 gene.

The invention also encompasses a method for sub-grouping animals according to genotype wherein the animals of each sub-group have a similar genotype in UCN3 gene which may comprise determining the genotype of each animal to be sub-grouped by determining the presence of a single nucleotide polymorphism(s) of interest in UCN3 gene, and segregating individual animals into sub-groups depending on whether the animals have, or do not have, the single nucleotide polymorphism(s) of interest in UCN3 gene.

The genetic polymorphism(s) of interest may be selected from the group consisting of AAFC03043460.1:g.8272-8281AATAATAAAT(SEQ ID NO: 9)>GGAGC, g.8208C>T, g.8265C>T, g.8287T>C, g.8412A>G, g.8426T>A, c.8786C>T, g.9074T>C, c.12609C>T, c.12621T>C, c.12667T>G and c.12669C>A.

The invention further relates to a method for sub-grouping animals according to genotype wherein the animals of each sub-group have a similar genotype in a UCN3 gene which may comprise determining the genotype of each animal to be sub-grouped by determining the presence of the above MNP and/or SNP, and segregating individual animals into sub-groups depending on whether the animals have, or do not have, the above MNP and/or SNP in a UCN3 gene.

The invention also relates to method for identifying an animal having a desirable phenotype as compared to the general population of animals of that species, which may comprise determining the presence of a single nucleotide polymorphism in a UCN3 gene of the animal, wherein the presence of the MNP and/or SNP is indicative of a desirable phenotype.

In an advantageous embodiment, the animal may be a bovine. In another advantageous embodiment, a UCN3 gene may be a bovine UCN3 gene.

The invention also encompasses computer-assisted methods and systems for improving the production efficiency for livestock having desirable intramuscular fat deposition and in particular the genotype of the animals as it relates to UCN3 MNPs and SNPs. Methods of the invention encompass obtaining a genetic sample from each animal in a herd of livestock, determining the genotype of each animal with respect to specific quality traits as defined by a panel of at least two multiple nucleotide polymorphisms (MNPs) or single polynucleotide polymorphisms (SNPs), grouping animals with like genotypes, and optionally, further sub-grouping animals based on like phenotypes. Methods of the invention may also encompass obtaining and maintaining data relating to the animals or to herds, their husbandry conditions, health and veterinary care and condition, genetic history or parentage, and providing this data to others through systems that are web-based, contained in a database, or attached to the animal itself such as by an implanted microchip. An advantageous aspect of the present invention, therefore, is directed to a computer system and computer-assisted methods for tracking quality traits for livestock possessing specific genetic predispositions.

The present invention advantageously encompasses computer-assisted methods and systems for acquiring genetic data, particularly genetic data as defined by the absence or presence of a MNP or SNP within a UCN3 gene related to intramuscular fat deposition of the breed of animal and associating those data with other data about the animal or its herd, and maintaining those data in ways that are accessible. Another aspect of the invention encompasses a computer-assisted method for predicting which livestock animals possess a biological difference in intramuscular fat deposition, and which may include the steps of using a computer system, e.g., a programmed computer comprising a processor, a data storage system, an input device and an output device, the steps of: (a) inputting into the programmed computer through the input device data that includes a genotype of an animal as it relates to any one of the UCN3 MNPs or SNPs described herein, (b) correlating intramuscular fat deposition predicted by the UCN3 genotype using the processor and the data storage system and (c) outputting to the output device the intramuscular fat deposition correlated to the UCN3 genotype, thereby predicting which livestock animals possess a particular intramuscular fat deposition.

Yet another aspect of the invention relates to a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals, wherein a physical characteristic intake, growth or carcass merit in beef cattle and the genotype is a UCN3 genotype.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 2 presents the nucleotide sequence of the proximal promoter region of the bovine UCN3 gene (SEQ ID NO: 7). Primer and partial non-coding exon 1 sequences are shadowed and underlined, respectively. The putative transcription start site is numbered as +1. Four polymorphic sites that were associated with SFD are bold and underlined. Potential transcription regulatory biding sites for TFCP2, NFAT5, NKX3-1, FOXD1, ISL1, DBP, CART1, POU4F1, ARID3A and MSX1/MSX2 are associated with haplotype CTAT, while only binding sites for BAPX1 and EGR2 are linked to haplotype TCGA.

FIGS. 4A-4D present the bovine UCN3 genomic DNA sequence (SEQ ID NO:8).>gi|112135004|gb|AAFC03043460.1| Bos taurus Ctg89.CH240-325G3, whole genome shotgun sequence. Mutations are bold underlined, primer biding sites are underlined and coding sequences are highlighted.

DETAILED DESCRIPTION

Figure 1:
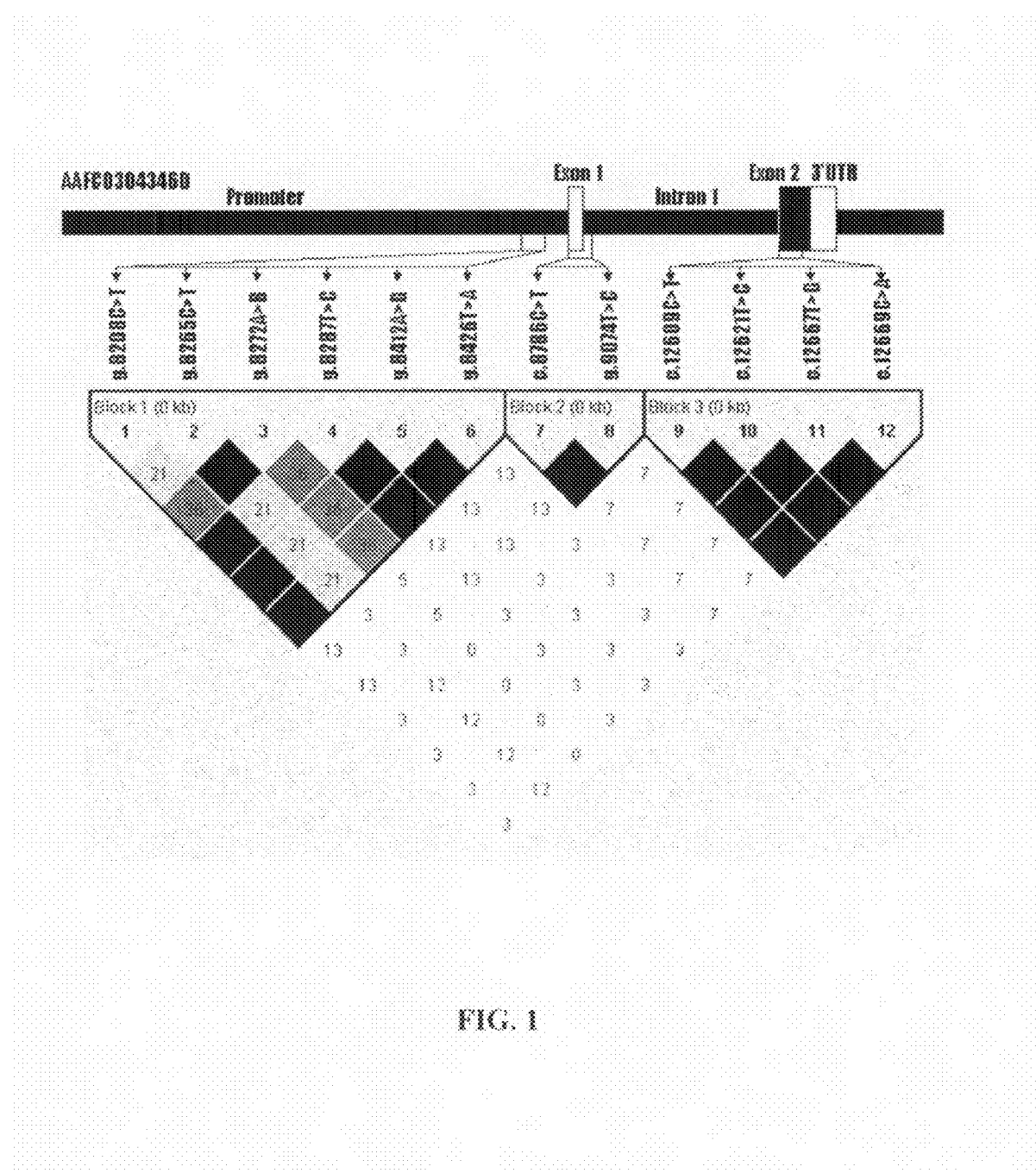
FIG. 1 presents genomic organization and haplotype analysis in the bovine UCN3 gene. Noncoding exon 1, partial non-coding exon 2 and 3'untranslated region are marked by white boxes and coding exon 2 by a black box. Pairwise linkage disequilibrium relationship for 12 mutations is illustrated based on $r^2$ measurements. The mutation g.8272A>B represents AAFC03043460.1:g.8272-8281AATAATAAAT (SEQ ID NO:9)>GGAGC.

Applicants hypothesized that urocortin 3 (UCN3) is associated with muscle fat deposition and subcutaneous fat depth (SFD) because the corticotropin-releasing hormone family of peptides are capable of strong anorectic and thermogenic effects.

The bovine UCN3 gene was annotated, and the Applicants identified 12 genetic mutations in the gene. Genotyping of these 12 markers on Wagyu x Limousin $F_2$ progeny revealed significant associations between promoter polymorphisms and SFD (P=0.0203-0.0685) and between missense mutations of exon 2 and marbling (P=0.0055-0.0369) in the bovine UCN3 gene. The SFD associated promoter SNPs caused a gain/loss of twelve potential transcription regulatory binding sites, while the marbling associated coding SNPs affected the secondary structure of UCN3 mRNA. Statistical analysis using the general linear model (GLM) procedure of SAS and quantitative transmission-disequilibrium test (QTDT) revealed that UCN3 gene is significantly associated with both marbling and subcutaneous lipid accumulation in Wagyu x Limousin $F_2$ crosses.

Applicants' cross species study provides further evidence that UCN3 is a likely target for developing antiobesity drugs, because it is located on human chromosome 10p15.1 where quantitative trait loci for obesity have been reported.

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook et al. (2001) Molecular Cloning: A Laboratory Manual, 3rd ed., Cold Spring Harbor Press; DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed and are intended to be defined as indicated below.

The term "cow" or "cattle" is used generally to refer to an animal of bovine origin of any age. Interchangeable terms include "bovine", "calf", "steer", "bull", "heifer" and the like. It also includes an individual animal in all stages of development, including embryonic and fetal stages. The animals as referred to herein may also include individuals or groups of individuals that are raised for other than food production such as, but not limited to, transgenic animals for the production of biopharmaceuticals including antibodies and other proteins or protein products.

By the term "complementarity" or "complementary" is meant, for the purposes of the specification or claims, a sufficient number in the oligonucleotide of complementary base pairs in its sequence to interact specifically (hybridize) with a target nucleic acid sequence of the gene polymorphism to be amplified or detected. As known to those skilled in the art, a very high degree of complementarity is needed for specificity and sensitivity involving hybridization, although it need not be 100%. Thus, for example, an oligonucleotide that is identical in nucleotide sequence to an oligonucleotide disclosed herein, except for one base change or substitution, may function equivalently to the disclosed oligonucleotides. A "complementary DNA" or "cDNA" gene includes recombinant genes synthesized by reverse transcription of messenger RNA ("mRNA").

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time.

By the term "detectable moiety" is meant, for the purposes of the specification or claims, a label molecule (isotopic or non-isotopic) which is incorporated indirectly or directly into an oligonucleotide, wherein the label molecule facilitates the detection of the oligonucleotide in which it is incorporated, for example when the oligonucleotide is hybridized to amplified gene polymorphic sequences. Thus, "detectable moiety" is used synonymously with "label molecule". Synthesis of oligonucleotides can be accomplished by any one of several methods known to those skilled in the art. Label molecules, known to those skilled in the art as being useful for detection, include chemiluminescent, fluorescent or luminescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule.

"DNA amplification" as used herein refers to any process that increases the number of copies of a specific DNA sequence by enzymatically amplifying the nucleic acid sequence. A variety of processes are known. One of the most commonly used is the polymerase chain reaction (PCR) process of Mullis as described in U.S. Pat. Nos. 4,683,195 and 4,683,202. Methods, devices and reagents as described in U.S. Pat. Nos. 6,951,726; 6,927,024; 6,924,127; 6,893,863; 6,887,664; 6,881,559; 6,855,522; 6,855,521; 6,849,430; 6,849,404; 6,846,631; 6,844,158; 6,844,155; 6,818,437; 6,818,402; 6,794,177; 6,794,133; 6,790,952; 6,783,940; 6,773,901; 6,770,440; 6,767,724; 6,750,022; 6,744,789;

6,733,999; 6,733,972; 6,703,236; 6,699,713; 6,696,277; 6,664,080; 6,664,064; 6,664,044; RE38,352; 6,650,719; 6,645,758; 6,645,720; 6,642,000; 6,638,716; 6,632,653; 6,617,107; 6,613,560; 6,610,487; 6,596,492; 6,586,250; 6,586,233; 6,569,678; 6,569,627; 6,566,103; 6,566,067; 6,566,052; 6,558,929; 6,558,909; 6,551,783; 6,544,782; 6,537,752; 6,524,830; 6,518,020; 6,514,750; 6,514,706; 6,503,750; 6,503,705; 6,493,640; 6,492,114; 6,485,907; 6,485,903; 6,482,588; 6,475,729; 6,468,743; 6,465,638; 6,465,637; 6,465,171; 6,448,014; 6,432,646; 6,428,987; 6,426,215; 6,423,499; 6,410,223; 6,403,341; 6,399,320; 6,395,518; 6,391,559; 6,383,755; 6,379,932; 6,372,484; 6,368,834; 6,365,375; 6,358,680; 6,355,422; 6,348,336; 6,346,384; 6,319,673; 6,316,195; 6,316,192; 6,312,930; 6,309,840; 6,309,837; 6,303,343; 6,300,073; 6,300,072; 6,287,781; 6,284,455; 6,277,605; 6,270,977; 6,270,966; 6,268,153; 6,268,143; D445,907; 6,261,431; 6,258,570; 6,258,567; 6,258,537; 6,258,529; 6,251,607; 6,248,567; 6,235,468; 6,232,079; 6,225,093; 6,221,595; D441,091; 6,218,153; 6,207,425; 6,183,999; 6,183,963; 6,180,372; 6,180,349; 6,174,670; 6,153,412; 6,146,834; 6,143,496; 6,140,613; 6,140,110; 6,103,468; 6,087,097; 6,072,369; 6,068,974; 6,063,563; 6,048,688; 6,046,039; 6,037,129; 6,033,854; 6,031,960; 6,017,699; 6,015,664; 6,015,534; 6,004,747; 6,001,612; 6,001,572; 5,985,619; 5,976,842; 5,972,602; 5,968,730; 5,958,686; 5,955,274; 5,952,200; 5,936,968; 5,909,468; 5,905,732; 5,888,740; 5,883,924; 5,876,978; 5,876,977; 5,874,221; 5,869,318; 5,863,772; 5,863,731; 5,861,251; 5,861,245; 5,858,725; 5,858,718; 5,856,086; 5,853,991; 5,849,497; 5,837,468; 5,830,663; 5,827,695; 5,827,661; 5,827,657; 5,824,516; 5,824,479; 5,817,797; 5,814,489; 5,814,453; 5,811,296; 5,804,383; 5,800,997; 5,780,271; 5,780,222; 5,776,686; 5,774,497; 5,766,889; 5,759,822; 5,750,347; 5,747,251; 5,741,656; 5,716,784; 5,712,125; 5,712,090; 5,710,381; 5,705,627; 5,702,884; 5,693,467; 5,691,146; 5,681,741; 5,674,717; 5,665,572; 5,665,539; 5,656,493; 5,656,461; 5,654,144; 5,652,102; 5,650,268; 5,643,765; 5,639,871; 5,639,611; 5,639,606; 5,631,128; 5,629,178; 5,627,054; 5,618,703; 5,618,702; 5,614,388; 5,610,017; 5,602,756; 5,599,674; 5,589,333; 5,585,238; 5,576,197; 5,565,340; 5,565,339; 5,556,774; 5,556,773; 5,538,871; 5,527,898; 5,527,510; 5,514,568; 5,512,463; 5,512,462; 5,501,947; 5,494,795; 5,491,225; 5,487,993; 5,487,985; 5,484,699; 5,476,774; 5,475,610; 5,447,839; 5,437,975; 5,436,144; 5,426,026; 5,420,009; 5,411,876; 5,393,657; 5,389,512; 5,364,790; 5,364,758; 5,340,728; 5,283,171; 5,279,952; 5,254,469; 5,241,363; 5,232,829; 5,231,015; 5,229,297; 5,224,778; 5,219,727; 5,213,961; 5,198,337; 5,187,060; 5,142,033; 5,091,310; 5,082,780; 5,066,584; 5,023,171 and 5,008,182 may also be employed in the practice of the present invention. PCR involves the use of a thermostable DNA polymerase, known sequences as primers, and heating cycles, which separate the replicating deoxyribonucleic acid (DNA), strands and exponentially amplify a gene of interest. Any type of PCR, such as quantitative PCR, RT-PCR, hot start PCR, LAPCR, multiplex PCR, touchdown PCR, etc., may be used. Advantageously, real-time PCR is used. In general, the PCR amplification process involves a cyclic enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

By the terms "enzymatically amplify" or "amplify" is meant, for the purposes of the specification or claims, DNA amplification, i.e., a process by which nucleic acid sequences are amplified in number. There are several means for enzymatically amplifying nucleic acid sequences. Currently the most commonly used method is the polymerase chain reaction (PCR). Other amplification methods include LCR (ligase chain reaction) which utilizes DNA ligase, and a probe consisting of two halves of a DNA segment that is complementary to the sequence of the DNA to be amplified, enzyme Qβ replicase and a ribonucleic acid (RNA) sequence template attached to a probe complementary to the DNA to be copied which is used to make a DNA template for exponential production of complementary RNA; strand displacement amplification (SDA); Qβ replicase amplification (QβRA); self-sustained replication (3SR); and NASBA (nucleic acid sequence-based amplification), which can be performed on RNA or DNA as the nucleic acid sequence to be amplified.

A "fragment" of a molecule such as a protein or nucleic acid is meant to refer to any portion of the amino acid or nucleotide genetic sequence.

As used herein, the term "genome" refers to all the genetic material in the chromosomes of a particular organism. Its size is generally given as its total number of base pairs. Within the genome, the term "gene" refers to an ordered sequence of nucleotides located in a particular position on a particular chromosome that encodes a specific functional product (e.g., a protein or RNA molecule). In general, an animal's genetic characteristics, as defined by the nucleotide sequence of its genome, are known as its "genotype," while the animal's physical traits are described as its "phenotype."

By "heterozygous" or "heterozygous polymorphism" is meant that the two alleles of a diploid cell or organism at a given locus are different, that is, that they have a different nucleotide exchanged for the same nucleotide at the same place in their sequences.

By "homozygous" or "homozygous polymorphism" is meant that the two alleles of a diploid cell or organism at a given locus are identical, that is, that they have the same nucleotide for nucleotide exchange at the same place in their sequences.

By "hybridization" or "hybridizing," as used herein, is meant the formation of A-T and C-G base pairs between the nucleotide sequence of a fragment of a segment of a polynucleotide and a complementary nucleotide sequence of an oligonucleotide. By complementary is meant that at the locus of each A, C, G or T (or U in a ribonucleotide) in the fragment sequence, the oligonucleotide sequenced has a T, G, C or A, respectively. The hybridized fragment/oligonucleotide is called a "duplex."

A "hybridization complex", such as in a sandwich assay, means a complex of nucleic acid molecules including at least the target nucleic acid and a sensor probe. It may also include an anchor probe.

As used herein, the term "locus" or "loci" refers to the site of a gene on a chromosome. Pairs of genes, known as "alleles" control the hereditary trait produced by a gene locus. Each animal's particular combination of alleles is referred to as its "genotype". Where both alleles are identical the individual is said to be homozygous for the trait controlled by that gene pair; where the alleles are different, the individual is said to be heterozygous for the trait.

A "melting temperature" is meant the temperature at which hybridized duplexes dehybridize and return to their single-stranded state. Likewise, hybridization will not occur in the first place between two oligonucleotides, or, herein, an oligonucleotide and a fragment, at temperatures above the melting temperature of the resulting duplex. It is presently advantageous that the difference in melting point temperatures of oligonucleotide-fragment duplexes of this invention be from about 1° C. to about 10° C. so as to be readily detectable.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but advantageously is double-stranded DNA. "DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). An "isolated" nucleic acid molecule is one that is separated from other nucleic acid molecules that are present in the natural source of the nucleic acid.

A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

A "polymerase" is an enzyme that catalyzes the sequential addition of monomeric units to a polymeric chain, or links two or more monomeric units to initiate a polymeric chain. The "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary strands using two primers. A "thermostable polymerase" refers to a DNA or RNA polymerase enzyme that can withstand extremely high temperatures, such as those approaching 100° C. Often, thermostable polymerases are derived from organisms that live in extreme temperatures, such as *Thermus aquaticus*. Examples of thermostable polymerases include Taq, Tth, Pfu, Vent, deep vent, UlTma, and variations and derivatives thereof.

A "polynucleotide" refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides linked by a phosphodiester backbone. A "modified polynucleotide" refers to a polynucleotide in which one or more natural nucleotides have been partially, substantially, or completely replaced with modified nucleotides.

A "primer" is an oligonucleotide, the sequence of at least of portion of which is complementary to a segment of a template DNA which is to be amplified or replicated. Typically primers are used in performing the polymerase chain reaction (PCR). A primer hybridizes with (or "anneals" to) the template DNA and is used by the polymerase enzyme uses as the starting point for the replication/amplification process. The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

"Probes" refer to oligonucleotides nucleic acid sequences of variable length, used in the detection of identical, similar, or complementary nucleic acid sequences by hybridization. An oligonucleotide sequence used as a detection probe may be labeled with a detectable moiety.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially pure of the materials with which it is associated in its native environment. By substantially free, is meant at least 50%, at least 55%, at least 60%, at least 65%, at advantageously at least 70%, at least 75%, more advantageously at least 80%, at least 85%, even more advantageously at least 90%, at least 91%, at least 92%, at least 93%, at least 94%, at least 95%, at least 96%, at least 97%, most advantageously at least 98%, at least 99%, at least 99.5%, at least 99.9% free of these materials.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

The term "polynucleotide encoding a protein" as used herein refers to a DNA fragment or isolated DNA molecule encoding a protein, or the complementary strand thereto; but, RNA is not excluded, as it is understood in the art that thymidine (T) in a DNA sequence is considered equal to uracil (U) in an RNA sequence. Thus, RNA sequences for use in the invention, e.g., for use in RNA vectors, can be derived from DNA sequences, by thymidine (T) in the DNA sequence being considered equal to uracil (U) in RNA sequences.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence.

"Homology" refers to the percent identity between two polynucleotide or two polypeptide moieties. Two DNA, or two polypeptide sequences are "substantially homologous" to each other when the sequences exhibit at least about 80%, 81%, 82%, 83%, 84%, 85%, 86%, 87%, 88%, 89%, preferably at least about 90%, 91%, 92%, 93%, 94% and most preferably at least about 95%, 96%, 97%, 98%, 99%, 99.5%, 99.9% sequence identity over a defined length of the molecules. As used herein, substantially homologous also refers to sequences showing complete identity (100% sequence identity) to the specified DNA or polypeptide sequence.

Homology can be determined by hybridization of polynucleotides under conditions that form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al. supra; DNA Cloning, supra; Nucleic Acid Hybridization, supra.

Two nucleic acid fragments are considered to be "selectively hybridizable" to a polynucleotide if they are capable of specifically hybridizing to a nucleic acid or a variant thereof or specifically priming a polymerase chain reaction: (i) under typical hybridization and wash conditions, as described, for example, in Sambrook et al. supra and Nucleic Acid Hybridization, supra, (ii) using reduced stringency wash conditions that allow at most about 25-30% basepair mismatches, for example: 2×SSC, 0.1% SDS, room temperature twice, 30 minutes each; then 2×SSC, 0.1% SDS, 37° C. once, 30 minutes; then 2×SSC room temperature twice, 10 minutes each, or (iii) selecting primers for use in typical polymerase chain reactions (PCR) under standard conditions (described for example, in Saiki, et al. (1988) Science 239:487-491).

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a nucleic acid or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° Celsius in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. (2001) Molecular Cloning: A Laboratory Manual, 3rd ed., Cold Spring Harbor Press, the contents of which are herein incorporated by reference in their entirety.

Typically, stringent conditions will be those in which the salt concentration is less than about 1.5 M sodium ion, typically about 0.01 to 1.0 M Na ion concentration (or other salts) from about pH 7.0 to about pH 8.3 and the temperature is at least about 30° Celsius for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1-2×SSC at 50 to 55° Celsius. Exemplary moderate stringency conditions include hybridization in 40 to 45% formamide, 1 M NaCl, 1% SDS at 37° Celsius, and a wash in 0.5-1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

Methods and materials of the invention may be used more generally to evaluate a DNA sample from an animal, genetically type an individual animal, and detect genetic differences in animals. In particular, a sample of genomic DNA from an animal may be evaluated by reference to one or more controls to determine if a MNP or SNP, or group of MNPs or SNPs, in a gene is present. Any method for determining genotype can be used for determining the genotype in the present invention. Such methods include, but are not limited to, amplimer sequencing, DNA sequencing, fluorescence spectroscopy, fluorescence resonance energy transfer (or "FRET")-based hybridization analysis, high throughput screening, mass spectroscopy, microsatellite analysis, nucleic acid hybridization, polymerase chain reaction (PCR), RFLP analysis and size chromatography (e.g., capillary or gel chromatography), all of which are well known to one of skill in the art. In particular, methods for determining nucleotide polymorphisms, particularly single nucleotide polymorphisms, are described in U.S. Pat. Nos. 6,514,700; 6,503,710; 6,468,742; 6,448,407; 6,410,231; 6,383,756; 6,358,679; 6,322,980; 6,316,230; and 6,287,766 and reviewed by Chen and Sullivan, Pharmacogenomics J 2003; 3(2):77-96, the disclosures of which are incorporated by reference in their entireties. Genotypic data useful in the methods of the invention and methods for the identification and selection of animal traits are based on the presence of MNPs and/or SNPs.

A "restriction fragment" refers to a fragment of a polynucleotide generated by a restriction endonuclease (an enzyme that cleaves phosphodiester bonds within a polynucleotide chain) that cleaves DNA in response to a recognition site on the DNA. The recognition site (restriction site) consists of a specific sequence of nucleotides typically about 4-8 nucleotides long.

A "single nucleotide polymorphism" or "SNP" refers to a variation in the nucleotide sequence of a polynucleotide that differs from another polynucleotide by a single nucleotide difference. For example, without limitation, exchanging one A for one C, G or T in the entire sequence of polynucleotide constitutes a SNP. It is possible to have more than one SNP in a particular polynucleotide. For example, at one position in a polynucleotide, a C may be exchanged for a T, at another position a G may be exchanged for an A and so on. When referring to SNPs, the polynucleotide is most often DNA.

As used herein, a "template" refers to a target polynucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such a DNA strand may be single-stranded or it may be part of a double-stranded DNA template. In applications of the present invention requiring repeated cycles of polymerization, e.g., the polymerase chain reaction (PCR), the template strand itself may become modified by incorporation of modified nucleotides, yet still serve as a template for a polymerase to synthesize additional polynucleotides.

A "thermocyclic reaction" is a multi-step reaction wherein at least two steps are accomplished by changing the temperature of the reaction.

A "variance" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variance" are used interchangeably herein. As used herein, the term "variance" in the singular is to be construed to include multiple variances; i.e., two or more nucleotide additions, deletions and/or substitutions in the same polynucleotide. A "point mutation" refers to a single substitution of one nucleotide for another.

As used herein, the terms "traits", "quality traits" or "physical characteristics" or "phenotypes" refer to advantageous properties of the animal resulting from genetics. Quality traits include, but are not limited to, the animal's genetic ability to efficiently metabolize energy, produce meat or milk, put on intramuscular fat. Physical characteristics include, but are not limited to, marbled, tender or lean meats. The terms may be used interchangeably.

A "computer system" refers to the hardware means, software means and data storage means used to compile the data of the present invention. The minimum hardware means of computer-based systems of the invention may comprise a central processing unit (CPU), input means, output means, and data storage means. Desirably, a monitor is provided to visualize structure data. The data storage means may be RAM or other means for accessing computer readable media of the invention. Examples of such systems are microcomputer workstations available from Silicon Graphics Incorporated and Sun Microsystems running Unix based, Linux, Windows NT, XP or IBM OS/2 operating systems.

"Computer readable media" refers to any media which can be read and accessed directly by a computer, and includes, but is not limited to: magnetic storage media such as floppy discs, hard storage medium and magnetic tape; optical storage media such as optical discs or CD-ROM; electrical storage media such as RAM and ROM; and hybrids of these categories, such as magnetic/optical media. By providing such computer readable media, the data compiled on a particular animal can be routinely accessed by a user, e.g., a feedlot operator.

The term "data analysis module" is defined herein to include any person or machine, individually or working together, which analyzes the sample and determines the genetic information contained therein. The term may include a person or machine within a laboratory setting.

As used herein, the term "data collection module" refers to any person, object or system obtaining a tissue sample from an animal or embryo. By example and without limitation, the term may define, individually or collectively, the person or machine in physical contact with the animal as the sample is taken, the containers holding the tissue samples, the packaging used for transporting the samples, and the like. Advantageously, the data collector is a person. More advantageously, the data collector is a livestock farmer, a breeder or a veterinarian The term "network interface" is defined herein to include any person or computer system capable of accessing data, depositing data, combining data, analyzing data, searching data, transmitting data or storing data. The term is broadly defined to be a person analyzing the data, the electronic hardware and software systems used in the analysis, the databases storing the data analysis, and any storage media capable of storing the data. Non-limiting examples of network interfaces include people, automated laboratory equipment, computers and computer networks, data storage devices such as, but not limited to, disks, hard drives or memory chips.

The term "breeding history" as used herein refers to a record of the life of an animal or group of animals including, but not limited to, the location, breed, period of housing, as well as a genetic history of the animals, including parentage and descent therefrom, genotype, phenotype, transgenic history if relevant and the like.

The term "husbandry conditions" as used herein refers to parameters relating to the maintenance of animals including, but not limited to, shed or housing temperature, weekly mortality of a herd, water consumption, feed consumption, ventilation rate and quality, litter condition and the like.

The term "veterinary history" as used herein refers to vaccination data of an animal or group of animals, including, but not limited to, vaccine type(s), vaccine batch serial number(s), administered dose, target antigen, method of administering of the vaccine to the recipient animal(s), number of vaccinated animals, age of the animals and the vaccinator. Data relating to a serological or immunological response induced by the vaccine may also be included. "Veterinary history" as used herein is also intended to include the medication histories of the target animal(s) including, but not limited to drug and/or antibiotics administered to the animals including type of administered medication, quantity and dose rates, by whom and when administered, by what route, e.g., oral, subcutaneously and the like, and the response to the medication including desired and undesirable effects thereof.

The term "diagnostic data" as used herein refers to data relating to the health of the animal(s) other than data detailing the vaccination or medication history of the animal(s). For example, the diagnostic data may be a record of the infections experienced by the animal(s) and the response thereof to medications provided to treat such medications. Serological data including antibody or protein composition of the serum or other biofluids may also be diagnostic data useful to input in the methods of the invention. Surgical data pertaining to the animal(s) may be included, such as the type of surgical manipulation, outcome of the surgery and complications arising from the surgical procedure. "Diagnostic data" may also include measurements of such parameters as weight, morbidity, and other characteristics noted by a veterinary service such as the condition of the skin, feet, etc.

The term "welfare data" as used herein refers to the collective accumulation of data pertaining to an animal or group of animals including, but not limited to, a breeding history, a veterinary history, a welfare profile, diagnostic data, quality control data, or any combination thereof.

The term "welfare profile" as used herein refers to parameters such as weight, meat density, crowding levels in breeding or rearing enclosures, psychological behavior of the animal, growth rate and quality and the like.

The term "quality control" as used herein refers to the desired characteristics of the animal(s). For non-poultry animals such as cattle and sheep for example, such parameters include muscle quantity and density, fat content, meat tenderness, milk yield and quality, breeding ability, and the like.

The term "performance parameters" as used herein refers to such factors as beef marbling, subcutaneous fat, meat yield, breeding yield, dairy form, meat quality and yield, daughter pregnancy rate (i.e., fertility), productive life (i.e., longevity) and the like that may be the desired goals from the breeding and rearing of the animal(s). Performance parameters may be either generated from the animals themselves, or those parameters desired by a customer or the market.

The term "nutritional data" as used herein refers to the composition, quantity and frequency of delivery of feed, including water, provided to the animal(s).

The term "food safety" as used herein refers to the quality of the meat from a livestock animal, including, but not limited to, preparation time, place and manner, storage of the food product, transportation route, inspection records, texture, color, taste, odor, bacterial content, parasitic content and the like.

It will be apparent to those of skill in the art that the data relating to the health and maintenance of the animals may be variously grouped depending upon the source or intention of the data collector and any one grouping herein is not therefore intended to be limiting.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

In an embodiment wherein the gene of interest is bovine UCN3, the bovine UCN3 nucleotide sequence can be selected from, but is not limited to, the sequence corresponding to GenBank Accession No. AAFC03043460.1 or a fragment thereof or a region of the bovine genome that comprises this sequence.

The present invention, therefore, provides isolated nucleic acids that may specifically hybridize to the nucleotide sequence can be selected from, but is not limited to, the sequence corresponding to GenBank Accession No. AAFC03043460.1 or the complement thereof, and which comprises the polymorphic sites corresponding to the UCN3 MNPs and SNPs.

The genetic polymorphism(s) of interest may be selected from the group consisting of AAFC03043460.1:g.8272-8281AATAATAAAT(SEQ ID NO:9)>GGAGC, g.8208C>T, g.8265C>T, g.8287T>C, g.8412A>G, g.8426T>A, c.8786C>T, g.9074T>C, c.12609C>T, c.12621T>C, c.12667T>G and c.12669C>A. The MNPs and SNPs advantageous in the present invention are associated with certain economically valuable and heritable traits relating to intramuscular fat deposition/marbling and subcutaneous fat depth in bovines. Therefore, it is an object of the present invention to determine the genotype of a given animal of interest as defined by the UCN3 locus MNP or SNP according to the present invention. It is also contemplated that the genotype of the animal(s) may be defined by additional MNPs or SNPs within the UCN3 gene or within other genes identified with desirable traits or other characteristics, and in particular by a panel or panels of MNPs and SNPs.

There are many methods known in the art for determining the sequence of DNA in a sample, and for identifying whether a given DNA sample contains a particular MNP or SNP. Any such technique known in the art may be used in performance of the methods of the present invention.

The methods of the present invention allow animals with certain economically valuable heritable traits to be identified based on the presence of MNPs and SNPs in their genomes and particularly MNPs and SNPs of the UCN3 gene. The methods further allow, by computer-assisted methods of the invention, to correlate the MNP- and SNP-associated traits with other data pertinent to the well-being and productive capacity of the animals, or group of animals.

To determine the genotype of a given animal according to the methods of the present invention, it is necessary to obtain a sample of genomic DNA from that animal. Typically, that sample of genomic DNA will be obtained from a sample of tissue or cells taken from that animal. A tissue or cell sample may be taken from an animal at any time in the lifetime of an animal but before the carcass identity is lost. The tissue sample can comprise hair, including roots, hide, bone, buccal swabs, blood, saliva, milk, semen, embryos, muscle or any internal organs. In the methods of the present invention, the source of the tissue sample, and thus also the source of the test nucleic acid sample, is not critical. For example, the test nucleic acid can be obtained from cells within a body fluid of the animal, or from cells constituting a body tissue of the animal. The particular body fluid from which cells are obtained is also not critical to the present invention. For example, the body fluid may be selected from the group consisting of blood, ascites, pleural fluid and spinal fluid. Furthermore, the particular body tissue from which cells are obtained is also not critical to the present invention. For example, the body tissue may be selected from the group consisting of skin, endometrial, uterine and cervical tissue. Both normal and tumor tissues can be used.

Typically, the tissue sample is marked with an identifying number or other indicia that relates the sample to the individual animal from which the sample was taken. The identity of the sample advantageously remains constant throughout the methods and systems of the invention thereby guaranteeing the integrity and continuity of the sample during extraction and analysis. Alternatively, the indicia may be changed in a regular fashion that ensures that the data, and any other associated data, can be related back to the animal from which the data was obtained.

The amount/size of sample required is known to those skilled in the art and for example, can be determined by the subsequent steps used in the method and system of the invention and the specific methods of analysis used. Ideally, the size/volume of the tissue sample retrieved should be as consistent as possible within the type of sample and the species of animal. For example, for cattle, non-limiting examples of sample sizes/methods include non-fatty meat: 0.0002 gm-10.0 gm; hide: 0.0004 gm-10.0 gm; hair roots: at least one and advantageously greater than five; buccal swabs: 15 to 20 seconds of rubbing with modest pressure in the area between outer lip and gum using, for example, a cytology brush; bone: 0.0002 gm-10.0 gm; blood: 30 µl to 50 ml.

Generally, the tissue sample is placed in a container that is labeled using a numbering system bearing a code corresponding to the animal, for example, to the animal's ear tag. Accordingly, the genotype of a particular animal is easily traceable at all times. The sampling device and/or container may be supplied to the farmer, a slaughterhouse or retailer. The sampling device advantageously takes a consistent and reproducible sample from individual animals while simultaneously avoiding any cross-contamination of tissue. Accordingly, the size and volume of sample tissues derived from individual animals would be consistent.

DNA can be isolated from the tissue/cells by techniques known to those skilled in the art (see, e.g., U.S. Pat. Nos. 6,548,256 and 5,989,431; Hirota et al. (1989) Jinrui Idengaku Zasshi. 34: 217-23 and John et al. (1991) Nucleic Acids Res. 19:408, the disclosures of which are incorporated by reference in their entireties). For example, high molecular weight DNA may be purified from cells or tissue using proteinase K extraction and ethanol precipitation. DNA, however, may be extracted from an animal specimen using any other suitable methods known in the art.

In one embodiment, the presence or absence of the MNP or SNP of any of the genes of the present invention may be determined by sequencing the region of the genomic DNA sample that spans the polymorphic locus. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the MNP or SNP of interest can be amplified using the polymerase chain reaction. The amplified region of DNA form can then be sequenced using any method known in the art, for example using an automatic nucleic acid sequencer. The detection of a given MNP or SNP can then be performed using hybridization of probes and or using PCR-based amplification methods. Such methods are described in more detail below.

The methods of the present invention may use oligonucleotides useful as primers to amplify specific nucleic acid sequences of the UCN3 gene, advantageously of the region encompassing a UCN3 MNP or SNP. Such fragments should be of sufficient length to enable specific annealing or hybridization to the nucleic acid sample. The sequences typically will be about 8 to about 44 nucleotides in length. Longer sequences, e.g., from about 14 to about 50, may be advantageous for certain embodiments. The design of primers is well known to one of ordinary skill in the art.

Inventive nucleic acid molecules include nucleic acid molecules having at least 70% identity or homology or similarity with a UCN3 gene or probes or primers derived therefrom such as at least 75% identity or homology or similarity, preferably at least 80% identity or homology or similarity, more preferably at least 85% identity or homology or similarity such as at least 90% identity or homology or similarity, more preferably at least 95% identity or homology or similarity such as at least 97% identity or homology or similarity. The nucleotide sequence similarity or homology or identity can be determined using the "Align" program of Myers and Miller, ("Optimal Alignments in Linear Space", CABIOS 4, 11-17, 1988) and available at NCBI. Alternatively or additionally, the terms "similarity" or "identity" or "homology", for instance, with respect to a nucleotide sequence, is intended to indicate a quantitative measure of homology between two sequences. The percent sequence similarity can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence similarity of 75% with the sequence AATCAATC ($N_{ref}=8$; $N_{dif}=2$). Alternatively or additionally, "similarity" with respect to sequences refers to the number of positions with identical nucleotides divided by the number of nucleotides in the shorter of the two sequences wherein alignment of the two sequences can be determined in accordance with the Wilbur and Lipman algorithm (Wilbur and Lipman, 1983 PNAS USA 80:726), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity with DNA sequences, thymidine (T) in the DNA sequence is considered equal to uracil (U) in the RNA sequence.

A probe or primer can be any stretch of at least 8, preferably at least 10, more preferably at least 12, 13, 14, or 15, such as at least 20, e.g., at least 23 or 25, for instance at least 27 or 30 nucleotides in a UCN3 gene which are unique to a UCN3 gene. As to PCR or hybridization primers or probes and optimal lengths therefor, reference is also made to Kajimura et al., GATA 7(4):71-79 (1990).

RNA sequences within the scope of the invention are derived from the DNA sequences, by thymidine (T) in the DNA sequence being considered equal to uracil (U) in RNA sequences.

The oligonucleotides can be produced by a conventional production process for general oligonucleotides. They can be produced, for example, by a chemical synthesis process or by a microbial process that makes use of a plasmid vector, a phage vector or the like. Further, it is suitable to use a nucleic acid synthesizer.

To label an oligonucleotide with the fluorescent dye, one of conventionally known labeling methods can be used (Tyagi & Kramer (1996) Nature Biotechnology 14: 303-308; Schofield et al. (1997) Appl. and Environ. Microbiol. 63: 1143-1147; Proudnikov & Mirzabekov (1996) Nucl. Acids Res. 24: 4532-4535). Alternatively, the oligonucleotide may be labeled with a radiolabel e.g., $^3H$, $^{125}I$, $^{35}S$, $^{14}C$, $^{32}P$, etc. Well-known labeling methods are described, for example, in Sambrook et al. (2001) Molecular Cloning: A Laboratory Manual, 3rd ed., Cold Spring Harbor Press. The label is coupled directly or indirectly to a component of the oligonucleotide according to methods well known in the art. Reversed phase chromatography or the like used to provide a nucleic acid probe for use in the present invention can purify the synthesized oligonucleotide labeled with a marker. An advantageous probe form is one labeled with a fluorescent dye at the 3'- or 5'-end and containing G or C as the base at the labeled end. If the 5'-end is labeled and the 3'-end is not labeled, the OH group on the C atom at the 3'-position of the 3'-end ribose or deoxyribose may be modified with a phosphate group or the like although no limitation is imposed in this respect.

During the hybridization of the nucleic acid target with the probes, stringent conditions may be utilized, advantageously along with other stringency affecting conditions, to aid in the hybridization. Detection by differential disruption is particularly advantageous to reduce or eliminate slippage hybridization among probes and target, and to promote more effective hybridization. In yet another aspect, stringency conditions may be varied during the hybridization complex stability determination so as to more accurately or quickly determine whether a MNP or SNP is present in the target sequence.

One method for determining the genotype at the polymorphic gene locus encompasses obtaining a nucleic acid sample, hybridizing the nucleic acid sample with a probe, and disrupting the hybridization to determine the level of disruption energy required wherein the probe has a different disruption energy for one allele as compared to another allele. In one example, there can be a lower disruption energy, e.g., melting temperature, for an allele that harbors a cytosine residue at a polymorphic locus, and a higher required energy for an allele with a different residue at that polymorphic locus. This can be achieved where the probe has 100% homology with one allele (a perfectly matched probe), but has a single mismatch with the alternative allele. Since the perfectly matched probe is bound more tightly to the target DNA than the mis-matched probe, it requires more energy to cause the hybridized probe to dissociate.

In a further step of the above method, a second ("anchor") probe may be used. Generally, the anchor probe is not specific to either allele, but hybridizes regardless of what nucleotide is present at the polymorphic locus. The anchor probe does not affect the disruption energy required to disassociate the hybridization complex but, instead, contains a complementary label for using with the first ("sensor") probe.

Hybridization stability may be influenced by numerous factors, including thermoregulation, chemical regulation, as well as electronic stringency control, either alone or in combination with the other listed factors. Through the use of stringency conditions, in either or both of the target hybridization step or the sensor oligonucleotide stringency step, rapid completion of the process may be achieved. This is desirable to achieve properly indexed hybridization of the target DNA to attain the maximum number of molecules at a test site with an accurate hybridization complex. By way of example, with the use of stringency, the initial hybridization step may be completed in ten minutes or less, more advantageously five minutes or less, and most advantageously two minutes or less. Overall, the analytical process may be completed in less than half an hour.

In one mode, the hybridization complex is labeled and the step of determining the amount of hybridization includes detecting the amounts of labeled hybridization complex at the test sites. The detection device and method may include, but is not limited to, optical imaging, electronic imaging, imaging with a CCD camera, integrated optical imaging, and mass spectrometry. Further, the amount of labeled or unlabeled probe bound to the target may be quantified. Such quantification may include statistical analysis. The labeled portion of the complex may be the target, the stabilizer, the probe or the hybridization complex in toto. Labeling may be by fluorescent labeling selected from the group of, but not limited to, Cy3, Cy5, Bodipy Texas Red, Bodipy Far Red, Lucifer Yellow, Bodipy 630/650-X, Bodipy R6G-X and 5-CR 6G. Colormetric labeling, bioluminescent labeling and/or chemiluminescent labeling may further accomplish labeling. Labeling further may include energy transfer between molecules in the hybridization complex by perturbation analysis, quenching, electron transport between donor and acceptor molecules, the latter of which may be facilitated by double stranded match hybridization complexes. Optionally, if the hybridization complex is unlabeled, detection may be accomplished by measurement of conductance differential between double stranded and non-double stranded DNA. Further, direct detection may be achieved by porous silicon-based optical interferometry or by mass spectrometry. In using mass spectrometry no fluorescent or other label is necessary. Rather detection is obtained by extremely high levels of mass resolution achieved by direct measurement, for example, by time of flight (TOF) or by electron spray ionization (ESI). Where mass spectrometry is contemplated, probes having a nucleic acid sequence of 50 bases or less are advantageous.

The label may be amplified, and may include, for example, branched or dendritic DNA. If the target DNA is purified, it may be un-amplified or amplified. Further, if the purified target is amplified and the amplification is an exponential method, it may be, for example, PCR amplified DNA or strand displacement amplification (SDA) amplified DNA. Linear methods of DNA amplification such as rolling circle or transcriptional runoff may also be used.

Where it is desired to amplify a fragment of DNA that comprises a MNP or SNP according to the present invention, the forward and reverse primers may have contiguous stretches of about 8, 9, 10, 11, 12, 13, 14, 15, 16, 17, 18, 19, 20, 21, 22, 23, 24, 25, 26, 27, 28, 29, 30 or any other length up to and including about 50 nucleotides in length. The sequences to which the forward and reverse primers anneal are advantageously located on either side of the particular nucleotide position that is substituted in the MNP or SNP to be amplified.

A detectable label can be incorporated into a nucleic acid during at least one cycle of an amplification reaction. Spectroscopic, photochemical, biochemical, immunochemical, electrical, optical or chemical means can detect such labels. Useful labels in the present invention include fluorescent dyes (e.g., fluorescein isothiocyanate, Texas red, rhodamine, and the like), radiolabels (e.g., $^3$H, $^{125}$I, $^{35}$S, $^{14}$C, $^{32}$P, etc.), enzymes (e.g. horseradish peroxidase, alkaline phosphatase etc.) colorimetric labels such as colloidal gold or colored glass or plastic (e.g. polystyrene, polypropylene, latex, etc.) beads. The label is coupled directly or indirectly to a component of the assay according to methods well known in the art. As indicated above, a wide variety of labels are used, with the choice of label depending on sensitivity required, ease of conjugation with the compound, stability requirements, available instrumentation, and disposal provisions. Non-radioactive labels are often attached by indirect means. Polymerases can also incorporate fluorescent nucleotides during synthesis of nucleic acids.

Reagents allowing the sequencing of reaction products can be utilized herein. For example, chain-terminating nucleotides will often be incorporated into a reaction product during one or more cycles of a reaction. Commercial kits containing the reagents most typically used for these methods of DNA sequencing are available and widely used. PCR exonuclease digestion methods for DNA sequencing can also be used. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the MNP or SNP of interest can amplified using the polymerase chain reaction or some other cyclic polymerase mediated amplification reaction. The amplified region of DNA can then be sequenced using any method known in the art. Advantageously, the nucleic acid sequencing is by automated methods (reviewed by Meldrum, (2000) Genome Res. 10: 1288-303, the disclosure of which is incorporated by reference in its entirety), for example using a Beckman CEQ 8000 Genetic Analysis System (Beckman Coulter Instruments, Inc.). Methods for sequencing nucleic acids include, but are not limited to, automated fluorescent DNA sequencing (see, e.g., Watts & MacBeath, (2001) Methods Mol Biol. 167: 153-70 and MacBeath et al. (2001) Methods Mol Biol. 167:119-52), capillary electrophoresis (see, e.g., Bosserhoff et al. (2000) Comb Chem High Throughput Screen. 3: 455-66), DNA sequencing chips (see, e.g., Jain, (2000) Pharmacogenomics. 1: 289-307), mass spectrometry (see, e.g., Yates, (2000) Trends Genet. 16: 5-8), pyrosequencing (see, e.g., Ronaghi, (2001) Genome Res. 11: 3-11), and ultrathin-layer gel electrophoresis (see, e.g., Guttman & Ronai, (2000) Electrophoresis. 21: 3952-64), the disclosures of which are hereby incorporated by reference in their entireties. The sequencing can also be done by a commercial company. Examples of such companies include, but are not limited to, the University of Georgia Molecular Genetics Instrumentation Facility (Athens, Ga.) or SeqWright DNA Technologies Services (Houston, Tex.).

A MNP- or SNP-specific probe can also be used in the detection of the MNP or SNP in amplified specific nucleic acid sequences of the target gene, such as the amplified PCR products generated using the primers described above. In certain embodiments, these MNP or SNP-specific probes consist of oligonucleotide fragments. Advantageously, the fragments are of sufficient length to provide specific hybridization to the nucleic acid sample. The use of a hybridization probe of between 10 and 50 nucleotides in length allows the formation of a duplex molecule that is both stable and selective. Molecules having complementary sequences over stretches greater than 12 bases in length are generally advantageous, in order to increase stability and selectivity of the hybrid, and thereby improve the quality and degree of particular hybrid molecules obtained. One will generally prefer to design nucleic acid molecules having stretches of 16 to 24 nucleotides, or even longer where desired. A tag nucleotide region may be included, as at the 5' end of the primer that may provide a site to which an oligonucleotide sequencing primer may hybridize to facilitate the sequencing of multiple PCR samples.

The probe sequence must span the particular nucleotide position that may be substituted in the particular MNP or SNP to be detected. Advantageously, two or more different "allele-specific probes" may be used for analysis of a MNP or SNP, a first allele-specific probe for detection of one allele, and a second allele-specific probe for the detection of the alternative allele.

It will be understood that this invention is not limited to the particular primers and probes disclosed herein and is intended to encompass at least nucleic acid sequences that are hybridizable to the nucleotide sequence disclosed herein, the complement or a fragment thereof, or are functional sequence analogs of these sequences. It is also contemplated that a particular trait of an animal may be determined by using a panel of MNPs and/or SNPs associated with that trait. Several economically relevant traits may be characterized by the presence or absence of one or more MNPs and/or SNPs and by a plurality of MNPs and/or SNPs in different genes. One or more panels of MNPs and/or SNPs may be used in the methods of the invention to define the phenotypic profile of the subject animal.

Homologs (i.e., nucleic acids derived from other species) or other related sequences (e.g., paralogs) can be obtained under conditions of standard or stringent hybridization conditions with all or a portion of the particular sequence as a probe using methods well known in the art for nucleic acid hybridization and cloning.

The genetic markers, probes thereof, methods, and kits of the invention are also useful in a breeding program to select for breeding those animals having desirable phenotypes for various economically important traits, such as intramuscular fat deposition. Continuous selection and breeding of animals, such as livestock, that are at least heterozygous and advantageously homozygous for desirable alleles of the UCN3 gene polymorphic sites associated with economically relevant traits of growth, feed intake, efficiency and/or carcass merit, and reproduction and longevity would lead to a breed, line, or population having higher numbers of offspring with economically relevant traits of growth, feed intake, efficiency and carcass merit, and reproduction and longevity. Thus, the UCN3 MNPs and SNPs of the present invention can be used as a selection tool.

Desirable phenotypes include, but are not limited to, feed intake, growth rate, body weight, carcass merit and composition, and reproduction and longevity, and milk yield. Specific carcass traits with desirable phenotypes include, but are not limited to, additional carcass value (additional carc value, $), average daily gain (ADG, lb/d), backfat thickness (BFAT, in), calculated live weight (Calc Lv Wt, lb), calculated yield grade (cYG), days on feed (DOF, d), dressing percentage (DP, %), dry matter intake (DMI, lb), dry matter intake per day on feed (DMI per DOF, lb/d), hot carcass weight (HCW, lb), hot carcass weight value (HCW value, $), intramuscular fat content (IMF %, %), marbling score (MBS, 10 to 99), marbling score divided by days on feed (MBS/DOF), quality grade, less than or equal to select versus greater than or equal to choice (QG, <Se vs, >Ch), ribeye area (REA, in$^2$), ribeye area per hundred weight HCW (REA/cwt HCW, in$^2$/100 lb hot carcass weight (HCW) and marbling and/or subcutaneous fat depth (SFD).

One aspect of the present invention provides for grouping animals and methods for managing livestock production comprising grouping livestock animals such as cattle according the genotype as defined by panels of MNPs and/or SNPs, each panel comprising at least one SNP, one or more of which are in the UCN3 gene of the present invention. Other SNPs that may be included in panels of SNPs include, but not limited to, SNPs found in the CAST gene, the CRH gene, diacylglycerol O-acyltransferase (DGAT1) gene, DOPEY2 gene, GHR gene, FABP4 gene, ghrelin gene, KIAA1462 gene, leptin (LEP) gene, NPY gene, ob gene, PAPD1 gene, TFAM gene, and/or the UCP3 gene. The genetic selection and grouping methods of the present invention can be used in conjunction with other conventional phenotypic grouping methods such as grouping animals by visible characteristics such as weight, frame size, breed traits, and the like. The methods of the present invention provide for producing cattle having improved heritable traits, and can be used to optimize the performance of livestock herds in areas such as intramuscular fat deposition. The present invention provides methods of screening livestock to determine those more likely to develop a desired body condition by identifying the presence or absence of one or more gene polymorphisms correlated with intramuscular fat deposition.

As described above, and in the Examples, there are various phenotypic traits with which the MNPs and SNPs of the present invention may be associated. Each of the phenotypic and genetic traits can be tested using the methods described in the Examples, or using any suitable methods known in the art. Using the methods of the invention, a farmer, or feedlot operator, or the like, can group cattle according to each animal's genetic propensity for a desired trait such as growth rate, feed intake or feeding behavior, as determined by MNP and/or SNP genotype. The cattle are tested to determine homozygosity or heterozygosity with respect to the MNP or SNP alleles of one or more genes so that they can be grouped such that each pen contains cattle with like genotypes. Each pen of animals is then fed and otherwise maintained in a manner and for a time determined by the feedlot operator, and then slaughtered.

The individual genotypic data derived from a panel or panels of MNPs and SNPs for each animal or a herd of animals can be recorded and associated with various other data of the animal, e.g. health information, parentage, husbandry conditions, vaccination history, herd records, subsequent food safety data and the like. Such information can be forwarded to a government agency to provide traceability of an animal or meat product, or it may serve as the basis for breeding, feeding and marketing information. Once the data has or has not been associated with other data, the data is stored in an accessible database, such as, but not limited to, a computer database or a microchip implanted in the animal. The methods of the invention may provide an analysis of the input data that may be compared with parameters desired by the operator. These parameters include, but are not limited to, such as breeding goals, egg laying targets, vaccination levels of a herd. If the performance or properties of the animals deviates from the desired goals, the computer-based methods may trigger an alert to allow the operator to adjust vaccination doses, medications, feed etc accordingly.

The results of the analysis provide data that are associated with the individual animal or to the herd, in whole or in part, from which the sample was taken. The data are then kept in an accessible database, and may or may not be associated with other data from that particular individual or from other animals.

Data obtained from individual animals may be stored in a database that can be integrated or associated with and/or cross-matched to other databases. The database along with the associated data allows information about the individual animal to be known through every stage of the animal's life, i.e., from conception to consumption of the animal product.

The accumulated data and the combination of the genetic data with other types of data of the animal provides access to information about parentage, identification of herd, health information including vaccinations, exposure to diseases, feedlot location, diet and ownership changes. Information such as dates and results of diagnostic or routine tests are easily stored and attainable. Such information would be especially valuable to companies, particularly those who seek superior breeding lines.

Each animal may be provided with a unique identifier. The animal can be tagged, as in traditional tracing programs or have implant computer chips providing stored and readable data or provided with any other identification method which associates the animal with its unique identifier.

The database containing the MNP- and/or SNP-based genotype results for each animal or the data for each animal can be associated or linked to other databases containing data, for example, which may be helpful in selecting traits for grouping or sub-grouping of an animal. For example, and not for limitation, data pertaining to animals having particular vaccination or medication protocols, can optionally be further linked with data pertaining to animals having food from certain food sources. The ability to refine a group of animals is limited only by the traits sought and the databases containing information related to those traits.

Databases that can usefully be associated with the methods of the invention include, but are not limited to, specific or general scientific data. Specific data includes, but is not limited to, breeding lines, sires, dames, and the like, other animals' genotypes, including whether or not other specific animals possess specific genes, including transgenic genetic elements, location of animals which share similar or identical genetic characteristics, and the like. General data includes, but is not limited to, scientific data such as which genes encode for specific quality characteristics, breed association data, feed data, breeding trends, and the like.

One method of the present invention includes providing the animal owner or customer with sample collection equipment, such as swabs and tags useful for collecting samples from which genetic data may be obtained. Advantageously, the packaging is encoded with a bar code label. The tags are encoded with the same identifying indicia, advantageously with a matching bar code label. Optionally, the packaging contains means for sending the tags to a laboratory for analysis. The optional packaging is also encoded with identifying indicia, advantageously with a bar code label.

The method optionally includes a system wherein a database account is established upon ordering the sampling equipment. The database account identifier corresponds to the identifying indicia of the tags and the packaging. Upon shipment of the sampling equipment in fulfillment of the order, the identifying indicia are recorded in a database. Advantageously, the identifier is a bar code label which is scanned when the tags are sent. When the tags are returned to the testing facility, the identifier is again recorded and matched to the information previously recorded in the database upon shipment of the vial to the customer. Once the genotyping is completed, the information is recorded in the database and coded with the unique identifier. Test results are also provided to the customer or animal owner.

The data stored in the genotype database can be integrated with or compared to other data or databases for the purpose of identifying animals based on genetic propensities. Other data or databases include, but are not limited to, those containing information related to MNP- or SNP-based DNA testing, vaccination, Sure Health pre-conditioning program, estrus and pregnancy results, hormone levels, food safety/contamination, somatic cell counts, mastitis occurrence, diagnostic test results, milk protein levels, milk fat, vaccine status, health records, mineral levels, trace mineral levels, herd performance, and the like.

The present invention, therefore, encompasses computer-assisted methods for tracking the breeding and veterinary histories of livestock animals encompassing using a computer-based system comprising a programmed computer comprising a processor, a data storage system, an input device and an output device, and comprising the steps of generating a profile of a livestock animal by inputting into the programmed computer through the input device genotype data of the animal, wherein the genotype may be defined by a panel of at least two single nucleotide polymorphisms that predict at least one physical trait of the animal, inputting into the programmed computer through the input device welfare data of the animal, correlating the inputted welfare data with the phenotypic profile of the animal using the processor and the data storage system, and outputting a profile of the animal or group of animals to the output device.

The databases and the analysis thereof will be accessible to those to whom access has been provided. Access can be provided through rights to access or by subscription to specific portions of the data. For example, the database can be accessed by owners of the animal, the test site, the entity providing the sample to the test site, feedlot personnel, and veterinarians. The data can be provided in any form such as by accessing a website, fax, email, mailed correspondence, automated telephone, or other methods for communication. These data can also be encoded on a portable storage device, such as a microchip, that can be implanted in the animal. Advantageously, information can be read and new information added without removing the microchip from the animal.

The present invention comprises systems for performing the methods disclosed herein. Such systems comprise devices, such as computers, internet connections, servers, and storage devices for data. The present invention also provides for a method of transmitting data comprising transmission of information from such methods herein discussed or steps thereof, e.g., via telecommunication, telephone, video conference, mass communication, e.g., presentation such as a computer presentation (e.g., POWERPOINT), internet, email, documentary communication such as computer programs (e.g., WORD) and the like.

Systems of the present invention may comprise a data collection module, which includes a data collector to collect data from an animal or embryo and transmit the data to a data analysis module, a network interface for receiving data from the data analysis module, and optionally further adapted to combine multiple data from one or more individual animals, and to transmit the data via a network to other sites, or to a storage device.

More particularly, systems of the present invention comprise a data collection module, a data analysis module, a network interface for receiving data from the data analysis module, and optionally further adapted to combine multiple data from one or more individual animals, and to transmit the data via a network to other sites, and/or a storage device. For example, the data collected by the data collection module leads to a determination of the absence or presence of a MNP or SNP of a gene in the animal or embryo, and for example, such data is transmitted when the feeding regimen of the animal is planned.

In one embodiment where the data is implanted on a microchip on a particular animal, the farmer can optimize the efficiency of managing the herd because the farmer is able to identify the genetic predispositions of an individual animal as well as past, present and future treatments (e.g., vaccinations and veterinarian visits). The invention, therefore also provides for accessing other databases, e.g., herd data relating to genetic tests and data performed by others, by datalinks to other sites. Therefore, data from other databases can be transmitted to the central database of the present invention via a network interface for receiving data from the data analysis module of the other databases.

The invention relates to a computer system and a computer readable media for compiling data on an animal, the system containing inputted data on that animal, such as but not limited to, vaccination and medication histories, DNA testing, thyroglobulin testing, leptin testing, bovine spongiform encephalopathy (BSE) diagnosis, brucellosis vaccination, FMD (foot and mouth disease) vaccination, BVD (bovine viral diarrhea) vaccination, Sure Health pre-conditioning program, estrus and pregnancy results, tuberculosis, hormone levels, food safety/contamination, somatic cell counts, mastitis occurrence, diagnostic test results, milk protein levels, milk fat, vaccine status, health records, mineral levels, trace mineral levels, herd performance, and the like. The data of the animal can also include prior treatments as well as suggested tailored treatment depending on the genetic predisposition of that animal toward a particular disease.

The invention also provides for a computer-assisted method for improving animal production comprising using a computer system, e.g., a programmed computer comprising a processor, a data storage system, an input device and an output device, the steps of inputting into the programmed computer through the input device data comprising a breeding, veterinary, medication, diagnostic data and the like of an animal, correlating a physical characteristic predicted by the genotype using the processor and the data storage system, outputting to the output device the physical characteristic correlated to the genotype, and feeding the animal a diet based upon the physical characteristic, thereby improving livestock production.

The invention further provides for a computer-assisted method for optimizing efficiency of feedlots for livestock comprising using a computer system, e.g., a programmed computer comprising a processor, a data storage system, an input device and an output device, and the steps of inputting into the programmed computer through the input device data comprising a breeding, veterinary history of an animal, correlating the breeding, veterinary histories using the processor and the data storage system, outputting to the output device the physical characteristic correlated to the genotype, and feeding the animal a diet based upon the physical characteristic, thereby optimizing efficiency of feedlots for livestock.

The invention further comprehends methods of doing business by providing access to such computer readable media and/or computer systems and/or data collected from animals to users; e.g., the media and/or sequence data can be accessible to a user, for instance on a subscription basis, via the Internet or a global communication/computer network; or, the computer system can be available to a user, on a subscription basis.

In one embodiment, the invention provides for a computer system for managing livestock comprising physical characteristics and databases corresponding to one or more animals. In another embodiment, the invention provides for computer readable media for managing livestock comprising physical characteristics and veterinary histories corresponding to one or more animals. The invention further provides methods of doing business for managing livestock comprising providing to a user the computer system and media described above or physical characteristics and veterinary histories corresponding to one or more animals. The invention further encompasses methods of transmitting information obtained in any method or step thereof described herein or any information described herein, e.g., via telecommunications, telephone, mass communications, mass media, presentations, internet, email, etc.

The invention further encompasses kits useful for screening nucleic acid isolated from one or more bovine individuals for allelic variation of any one of the mitochondrial transcription factor genes, and in particular for any of the MNPs and SNPs described herein, wherein the kits may comprise at least one oligonucleotide selectively hybridizing to a nucleic acid comprising any one of the one or more of which are UCN3 sequences described herein and instructions for using the oligonucleotide to detect variation in the nucleotide corresponding to the MNP or SNP of the isolated nucleic acid.

One embodiment of this aspect of the invention provides an oligonucleotide that specifically hybridizes to the isolated nucleic acid molecule of this aspect of the invention, and wherein the oligonucleotide hybridizes to a portion of the isolated nucleic acid molecule comprising any one of the polymorphic sites in the UCN3 sequences described herein.

Another embodiment of the invention is an oligonucleotide that specifically hybridizes under high stringency conditions to any one of the polymorphic sites of the UCN3 gene, wherein the oligonucleotide is between about 18 nucleotides and about 50 nucleotides.

In another embodiment of the invention, the oligonucleotide comprises a central nucleotide specifically hybridizing with a UCN3 gene polymorphic site of the portion of the nucleic acid molecule.

Another aspect of the invention is a method of identifying a UCN3 polymorphism in a nucleic acid sample comprising isolating a nucleic acid molecule encoding UCN3 or a fragment thereof and determining the nucleotide at the polymorphic site.

Another aspect of the invention is a method of screening cattle to determine those bovines more likely to exhibit a biological difference in intramuscular fat deposition comprising the steps of obtaining a sample of genetic material from a bovine; and assaying for the presence of a genotype in the bovine which is associated with intramuscular fat deposition, the genotype characterized by a polymorphism in the bovine UCN3 gene.

In other embodiments of this aspect of the invention, the step of assaying is selected from the group consisting of: restriction fragment length polymorphism (RFLP) analysis, minisequencing, MALDI-TOF, SINE, heteroduplex analysis, single strand conformational polymorphism (SSCP), denaturing gradient gel electrophoresis (DGGE) and temperature gradient gel electrophoresis (TGGE).

In various embodiments of the invention, the method may further comprise the step of amplifying a region of the UCN3 gene or a portion thereof that contains the polymorphism. In other embodiments of the invention, the amplification may include the step of selecting a forward and a reverse sequence primer capable of amplifying a region of the UCN3 gene.

Another aspect of the invention is a computer-assisted method for predicting which livestock animals possess a biological difference in intramuscular fat deposition comprising: using a computer system, e.g., a programmed computer comprising a processor, a data storage system, an input device and an output device, the steps of: (a) inputting into the programmed computer through the input device data comprising a UCN3 genotype of an animal, (b) correlating intramuscular fat deposition predicted by the UCN3 genotype using the processor and the data storage system and (c) outputting to the output device the intramuscular fat deposition correlated to the UCN3 genotype, thereby predicting which livestock animals possess a particular intramuscular fat deposition.

Yet another aspect of the invention is a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals.

The invention will now be further described by way of the following non-limiting examples.

EXAMPLES

Example 1

This example demonstrates that the UCN3 gene is significantly associated with both marbling and subcutaneous lipid accumulation in Wagyu x Limousin $F_2$ crosses.

Materials and Methods

Animals and phenotypic traits. A Wagyu x Limousin reference population was developed, including 6 $F_1$ bulls, 113 $F_1$ dams and ~250 $F_2$ progeny (Jiang Z, Kunej T, Michal J J, Gaskins C T, Reeves J J et al. (2005) Significant associations of the mitochondrial transcription factor A promoter polymorphisms with marbling and subcutaneous fat depth in Wagyu x Limousin F2 crosses. Biochem Biophys Res Commun 334: 516-523). The Japanese Wagyu breed of +cattle has been traditionally selected for high muscle fat accumulation (measured as marbling score with an average of 8.52), whereas the Limousin breed has been selected for heavy muscle, which leads to low muscle fat accumulation (average marbling score less than 4.78) (Mir PS, Mir Z, Kubert PS, Gaskins CT, Martin EL et al. (2002) Growth, carcass characteristics, muscle conjugated linoleic acid (CLA) content, and response to intravenous glucose challenge in high percentage Wagyu, Wagyu x Limousin, and Limousin steers fed sunflower oil-containing diet. J Anim Sci 80: 2996-3004). The difference in marbling between these two breeds makes them very unique for mapping QTLs for the trait. Beef marbling score was a subjective measure of the amount of fat stored in the longissimus muscle based on published USDA standards. Subcutaneous fat depth (SFD) was measured at the 12-13$^{th}$ rib interface perpendicular to the outside surface at a point three-fourths the length of the longissimus muscle from its chine bone end. The marbling scores ranged from 4 to 9.5 and SFD varied from 0.1 to 1.3 inches in the population.

Sequence annotation and primer design. The genomic organization of bovine UCN3 was determined by aligning a bovine cDNA sequence (BC114855) with a bovine genomic DNA contig (AAFC03043460) retrieved from the GenBank database. Three pairs of primers were designed to target the promoter (forward—5'GGG GCT GCA CCA AGC AAA TGT CAA C3' (SEQ ID NO:1) and reverse—5'TCT ACC CTT CTT CCT GGA GCC AAC3' (SEQ ID NO:2)), non-coding exon 1 (forward—5'AGG TCT GGG AGA GAA GGT GGG TAG3' (SEQ ID NO:3) and reverse—5'AAA CAC AGA CAT TGA CGG TTC AGC3' (SEQ ID NO:4)) and coding exon 2 (forward—5'CTG AAC TTG CAC AAA GCC TGG TAG3' (SEQ ID NO:5) and reverse—5'CCC AGC CTC CTC CTC TAC TTC TTC3' (SEQ ID NO:6)) in the UCN3 gene.

Polymorphism detection and genotyping assay development. Approximately 50 ng of genomic DNA each from six $F_1$ bulls were amplified in a final volume of 10 μL that contained 12.5 ng of each primer, 150 μM dNTPs, 1.5 mM MgCl$_2$, 50 mM KCl, 20 mM Tris-HCl and 0.25 U of Platinum Taq polymerase (Invitrogen, Carlsbad, Calif.). The PCR conditions were carried out as follows: 94° C. for 2 min, 32 cycles of 94° C. for 30 sec, 63° C. for 30 sec and 72° C. for 30 sec, followed by a further 5 min extension at 72° C. PCR products were then sequenced for polymorphism detection on an ABI 3730 sequencer in the Laboratory for Biotechnology and Bioanalysis (Washington State University) using a standard protocol. The same PCR product direct sequencing approach was also used to genotype the polymorphisms on all animals.

Data analysis. The estimates for degrees of Hardy-Weinberg equilibrium within each mutation and linkage disequilibrium between mutations and selection of tagging genetic polymorphisms in bovine UCN3 gene were performed using the HAPLOVIEW program (Barrett J C, Fry B, Mailer J, Daly M J (2005) Haploview: analysis and visualization of LD and haplotype maps. Bioinformatics 21: 263-565). The phenotypic data for both marbling and SFD measurements were previously adjusted for year of birth, sex, age (days), live weight (kilograms), or fat depth (inches), as appropriate. The adjusted phenotypes were then used in a subsequent association analysis using the GLM (general linear model) procedure of SAS v9.1 (SAS institute Inc., Gary, N.C.). Pair-wise comparisons of least squares means were performed using a protected t-test. Additionally, quantitative transmission disequilibrium test (QTDT) (Abecasis G R, Cardon L R, Cookson W O (2000) A general test of association for quantitative traits in nuclear families. Am J Hum Genet 66: 279-292) was performed to further examine the association between the tagging mutations and adjusted obesity-related phenotype data. P value <0.05 was considered statistically significant after Bonferroni correction. For significantly associated mutations, the MatInspector web server (Quandt K, Frech K, Karas H, Wingender E, Werner T (1995) MatInd and MatInspector: new fast and versatile tools for detection of consensus matches in nucleotide sequence data. Nucleic Acids Res. 23: 4878-48) was used to screen potential transcriptional regulatory binding site changes caused by promoter polymorphisms, while the Mfold web server (Zuker M (2003) Mfold web server for nucleic acid folding and hybridization prediction. Nucleic Acids Res 31: 3406-3415) was used to predict mRNA secondary structure changes caused by coding polymorphisms.

Results

Genomic organization of the bovine UCN3 gene. BLAST searches using the cDNA sequence of the human UCN3 gene (NM_053049) as a reference retrieved three bovine orthologous cDNA sequences from the GenBank database. The longest cDNA sequence BC114855 with 1,404 bp was used and retrieved one genomic DNA sequence (AAFC03043460) of the same gene from the 7.15× bovine genome sequence database. Alignment of both cDNA and genomic DNA sequences determined the genomic organization of the bovine UCN3 gene. Like all four human CRH paralogs, the bovine UCN3 gene has two exons and one intron (FIG. 1).

Single and multiple nucleotide polymorphisms. In the bovine UCN3 gene, the promoter region harbors one multiple nucleotide polymorphism (MNP) and five single nucleotide polymorphisms (SNPs), while exons 1 and 2 contain two and four SNPs, respectively (FIG. 1). The MNP has two homozygous alleles of 10 bp and 5 bp, i.e., AAFC03043460.1: g.8272-8281AATAATAAAT(SEQ ID NO:9)>GGAGC. The remaining eleven SNPs are AAFC03043460.1:g.8208C>T, g.8265C>T, g.8287T>C, g.8412A>G, g.8426T>A, c.8786C>T, g.9074T>C, c.12609C>T, c.12621T>C, c.12667T>G and c.12669C>A, respectively (FIG. 1). Among these five coding SNPs, two (c.12667T>G and c.12669C>A) are missense mutations and both occur in one codon (codon 59), changing phenylalanine (TTC) to valine (GTA) at the preprohormone level of the UCN3 peptide. Haplotype analysis and selection of tagging mutations. In the bovine UCN3 gene, sequencing of 6 $F_1$ sires indicated that four SNPs in the promoter region: g.8208C>T, g.8287T>C, g.8412A>G and g.8426T>A form two haplotypes: CTAT and TCGA. Two SNPs in the exon 1 and flanking regions c.8784C>T and g.9072T>C also appear in two haplotypes: CC and TT in the population, while all four SNPs (c.12609C>T, c.12621T>C, c.12667T>G and c.12669C>A) in coding exon 2 region have no historical recombination in either CTTC or TCGA haplotypes. The lack of historical recombination among SNPs in each of these regions described above was further confirmed by the HAPLOVIEW program on genotype data of all $F_2$ progeny (FIG. 1). Therefore, g.8208C>T, g.8265C>T, g.8272-8281AATAATAAAT(SEQ ID NO:9)>GGAGC, c.8784C>T, and c.12669C>A were chosen as tagging mutations for association analysis.

Association analysis of UCN3 gene with marbling and SFD. Two statistical approaches—the general linear model (GLM) and the quantitative transmission disequilibrium test (QTDT) were used to detect associations of genetic polymorphisms in bovine UCN3 gene with marbling and SFD in a reference population of Wagyu x Limousin $F_2$ cross cattle (TABLE 1). Overall, the reference population had an average SFD of 0.394 inches with a standard deviation of 0.18 inches. In the bovine UCN3 gene, GLM analysis indicated a suggestive association between genotype at g.8208C>T and SFD (P=0.0685), while the QTDT test indicated a significant association between the genotype and SFD (P=0.0203; TABLE 1). Animals with TT genotypes had 0.086 (P=0.0045) and 0.056 inches (P=0.0259) less subcutaneous fat than animals with CC and CT genotypes, which account for 0.48 and 0.31 standard deviations for the trait, respectively (TABLE 1).

Overall, marbling scores for all $F_2$ progeny averaged 5.916 with a standard deviation of 1 marbling score. Interestingly, the genotype effects on this trait increased in significance with mutations closer to the coding regions of the UCN3 gene (TABLE 1). The 12669C>A marker was significantly associated with marbling (P=0.0369 for the GLM analysis and P=0.0055 for the QTDT test, respectively). AA animals were much leaner, with 0.549 and 0.340 lower marbling scores, respectively than CC animals (P=0.0045) and CT heterozygotes (P=0.0164) (TABLE 1).

Figure 2:
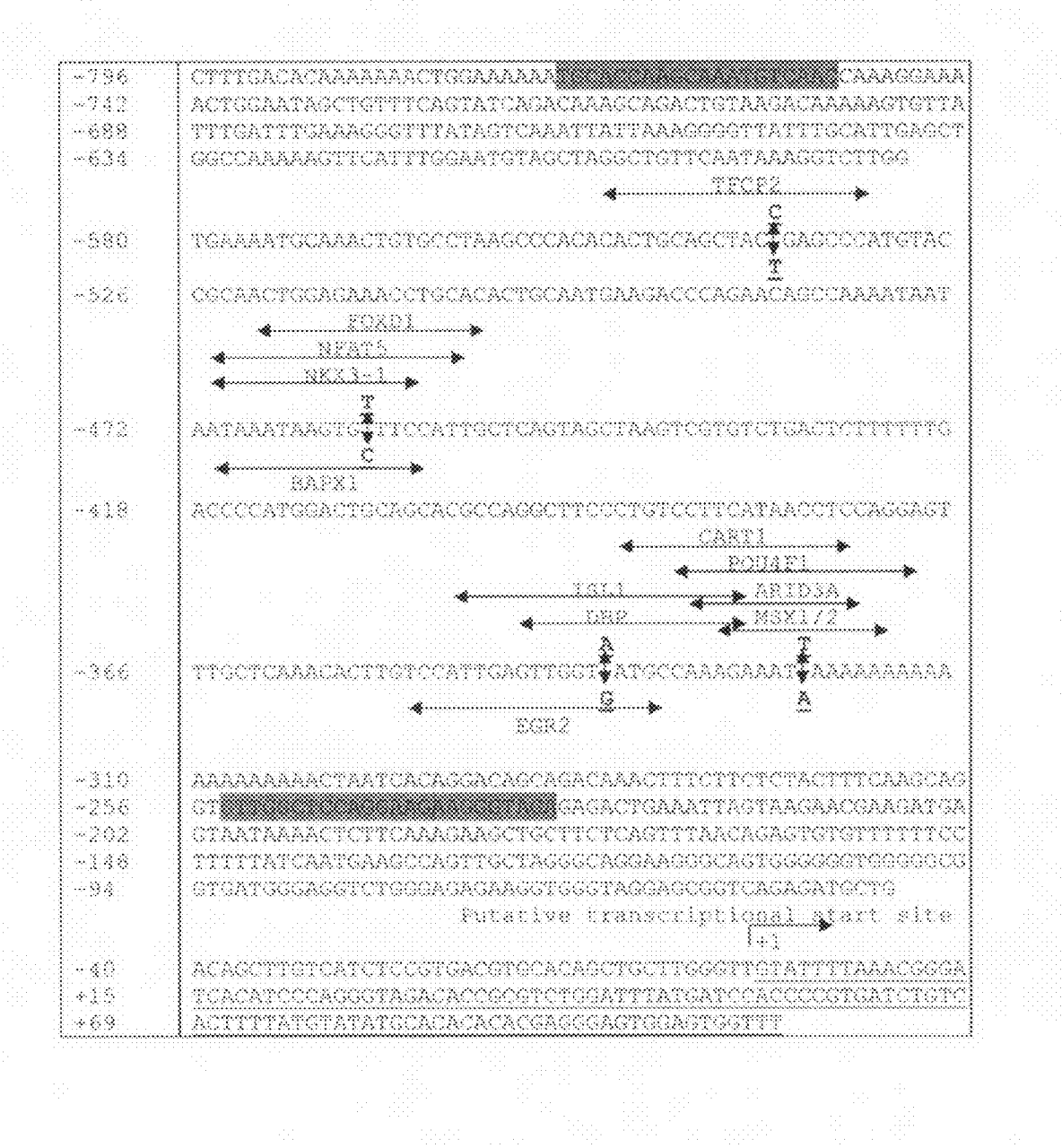

Functional characterization of promoter and coding polymorphisms associated with marbling and SFD. As indicated above, mutations in the bovine UCN3 gene were significantly associated with either trait in the reference population. Therefore, it might be interesting to characterize how the promoter polymorphisms affect transcriptional regulatory biding sites and how coding polymorphisms have an impact on the mRNA secondary structure. In the promoter region of the bovine UCN3 gene, four polymorphisms, AAFC03043460.1: g.8208C>T, g.8287T>C, g.8412A>G and g.8426T>A form two haplotypes: CTAT and TCGA. MatInspector (Quandt K, Frech K, Karas H, Wingender E, Werner T (1995) MatInd and MatInspector: new fast and versatile tools for detection of consensus matches in nucleotide sequence data. Nucleic Acids Res. 23: 4878-48) detected a remarkable difference in the number of potential transcriptional regulatory binding sites between these haplotypes: ten for the former haplotype, while only two for the latter haplotype (FIG. 2). These twelve transcriptional binding sites were for TFCP2 (transcription factor CP2), NFAT5 (nuclear factor of activated T-cells 5, tonicity-responsive), NKX3-1 (NK3 transcription factor related, locus 1), FOXD1 (forkhead box D1), BAPX1 (bagpipe homeobox homolog 1), ISL1 (ISL1 transcription factor, islet-1), DBP (D site of albumin promoter binding protein), EGR2 (early growth response 2), CART1 (cartilage paired-class homeoprotein 1), POU4μl (POU domain, class 4, transcription factor 1), ARID3A (AT rich interactive domain 3A) and MSX1 (msh homeobox homolog 1)/MSX2 (msh homeobox homolog 2), respectively (FIG. 2).

Figure 3:
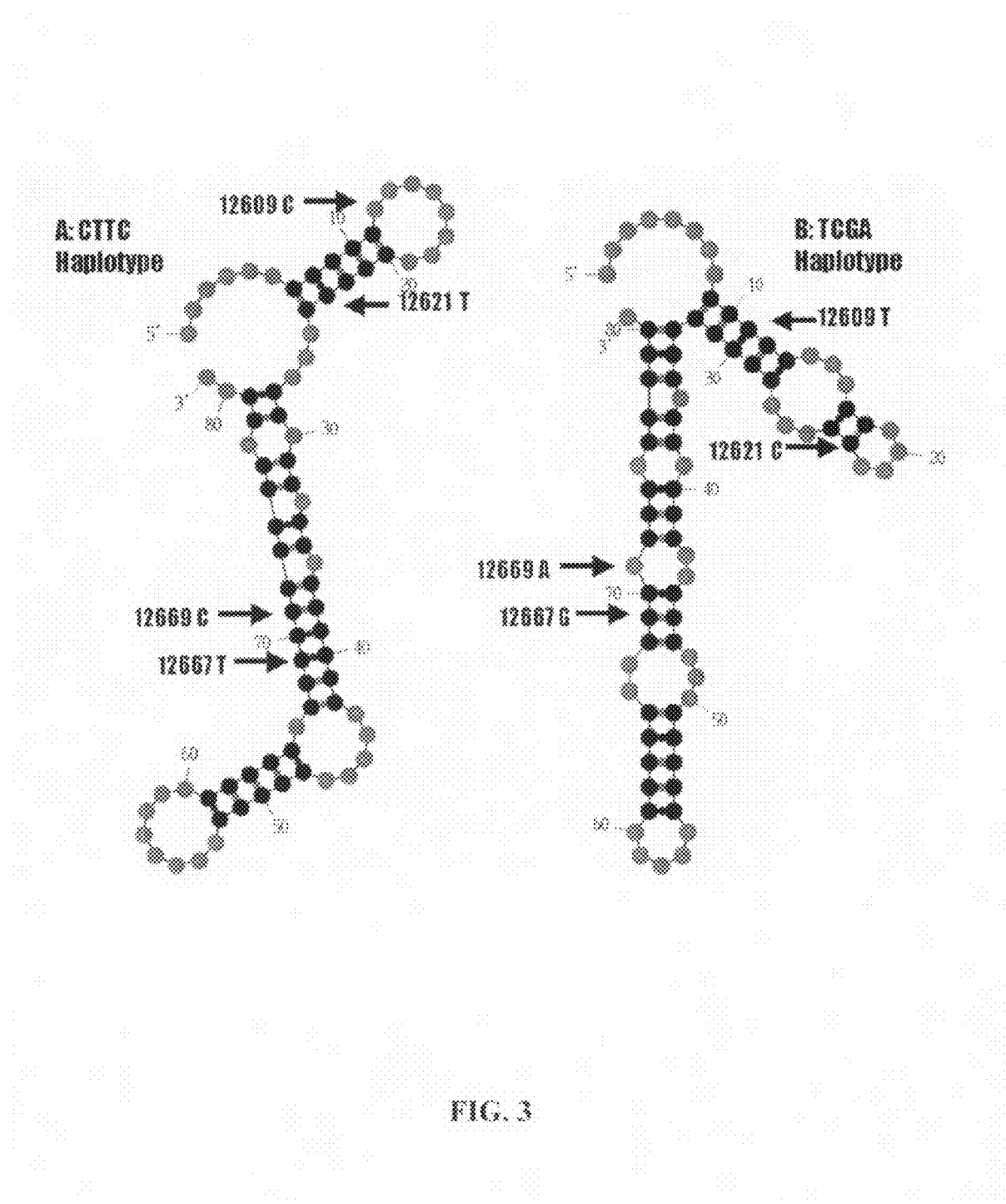
FIG. 3 presents UCN3 mRNA secondary structure predicted by Mfold on a partial sequence of 81 bp surrounding four coding SNPs. A: mRNA secondary structure for haplotype CTTC. B: mRNA secondary structure for haplotype TCGA.

Four coding SNPs in exon 2 of bovine UCN3 gene: AAFC03043460.1:c.12609C>T, c.12621T>C, c.12667T>G and c.12669C>A also form two haplotypes: CTTC or TCGA. We used the Mfold program (Zuker M (2003) Mfold web server for nucleic acid folding and hybridization prediction. Nucleic Acids Res 31: 3406-3415) to predict how these two haplotypes affect mRNA secondary structure. In the first run, a complete coding sequence of 501 bp for the preprohormone was used in the analysis. The sequences with both haplotypes were folded with Mfold in a locally automated manner. The complete coding sequence containing CTTC haplotype yielded a total of 13 secondary structures, while the sequence with the TCGA haplotype produced a total of 16 secondary structures. However, there was a difference in single-strandedness counts (ss-counts) between two haplotypes. The ss-counts measure the number of times each nucleotide is unpaired across all predicted secondary structures. For the former haplotype, 122 of 501 bp had zero ss-counts; while for the latter haplotype, 100 of 501 had zero ss-counts across all predicted secondary structures (Fisher's exact test, P=0.0150). In the second run, we selected 81 bp of sequence surrounding the SNPs for a more localized structure analysis. As showed in FIG. 3, both haplotypes had a strong effect on the secondary structure of bovine UCN3 mRNA.

types—TC and GA, showing no historical recombination in the population. Lastly, HAPLOVIEW analysis revealed that three amplified regions hold three haplotype blocks (FIG. 1); although the amplified promoter region and exon 1 region are just 147 bp apart and exon 1 and exon 2 regions are just 3,209 bp apart. These data might provide a foundation for further investigation on formation and evolution of CRH paralogs in mammals.

More importantly, Applicants found that the UCN3 gene is significantly associated with IMCL accumulation and SFD (TABLE 1). However, four promoter SNPs organized into two haplotypes had a strong association with SFD, while four SNPs which also formed two haplotypes in exon 2 yielded a strong association with muscle fat accumulation. In the SFD analysis, animals with TT genotypes of g.8208C>T had 0.086 (P=0.0045) and 0.056 inches (P=0.0259) less subcutaneous fat than animals with CC and CT genotypes, which account for 0.48 and 0.31 standard deviations for the trait. In the marbling analysis, AA animals at position c.12669C>A had 0.549 and 0.340 lower marbling scores than CC animals (P=0.0045) and CT heterozygotes (P=0.0164). On the other hand, the AA animals tended to be leaner with 0.047 and

TABLE 1

Associations of UCN3 gene with marbling and SFD

| | | | Marbling (in scores) | | | SFD (in inches) | | |
|---|---|---|---|---|---|---|---|---|
| Maker | Genotype | N | LSM ± S.E. | $P_{GLM}$ | $P_{QTDT}$ | LSM ± S.E. | $P_{GLM}$ | $P_{QTDT}$ |
| 8208C > T | CC | 52 | $5.925 \pm 0.135^a$ | 0.6180 | 0.7053 | $0.433 \pm 0.021^a$ | 0.0685 | 0.0203 |
| | CT | 132 | $5.986 \pm 0.084^a$ | | | $0.403 \pm 0.013^a$ | | |
| | TT | 54 | $5.695 \pm 0.132^a$ | | | $0.347 \pm 0.021^b$ | | |
| 8265C > T | CC | 158 | $5.931 \pm 0.077^a$ | 0.5138 | 0.8549 | $0.407 \pm 0.012^a$ | 0.8692 | 0.5785 |
| | CT | 75 | $5.920 \pm 0.112^{ab}$ | | | $0.375 \pm 0.018^a$ | | |
| | TT | 5 | $5.042 \pm 0.435^b$ | | | $0.383 \pm 0.070^a$ | | |
| 8272A > B* | AA | 122 | $5.802 \pm 0.087^a$ | 0.1981 | 0.8872 | $0.401 \pm 0.014^a$ | 0.9985 | 0.9739 |
| | AB | 102 | $6.081 \pm 0.095^b$ | | | $0.396 \pm 0.016^a$ | | |
| | BB | 14 | $5.577 \pm 0.259^{ab}$ | | | $0.365 \pm 0.042^a$ | | |
| 8786C > T | CC | 170 | $5.818 \pm 0.076^a$ | 0.1306 | 0.0629 | $0.393 \pm 0.012^a$ | 0.9977 | 0.9794 |
| | CT | 64 | $6.209 \pm 0.123^b$ | | | $0.412 \pm 0.020^a$ | | |
| | TT | 4 | $5.912 \pm 0.494^{ab}$ | | | $0.415 \pm 0.080^a$ | | |
| 12669C > A | AA | 84 | $5.665 \pm 0.107^a$ | 0.0369 | 0.0055 | $0.369 \pm 0.017^a$ | 0.4036 | 0.2351 |
| | CA | 114 | $6.005 \pm 0.092^b$ | | | $0.415 \pm 0.015^b$ | | |
| | CC | 38 | $6.214 \pm 0.159^b$ | | | $0.416 \pm 0.026^{ab}$ | | |

*See legends for FIG. 1.

Discussion

There are four paralogous corticotropin-releasing hormone genes in mammalian genomes: corticotropin-releasing hormone, urocortin, urocortin 2 and urocortin 3 (Bale TL, Vale WW (2004) CRF and CRF receptors: role in stress responsivity and other behaviors. Annu Rev Pharmacol Toxico 44: 525-557). In the present study, several interesting features about urocortin 3 in the bovine genome were revealed. First, the bovine UCN3 gene region seems highly polymorphic. Applicants designed three pairs of primers that amplified a total of 1,679 bp. A total of 12 mutations (one approximately every 140 bp of sequence) were detected in this region. Second, a multiple nucleotide polymorphism was detected in the promoter region of the bovine UCN3 gene. One allele has 10 nucleotides of AATAATAAAT(SEQ ID NO:9), while another has only five nucleotides of GGAGC. No significant similarity could be determined between these two alleles. Third, two SNPs (c.12667T>G and c.12669C>A) occurred in one codon (codon 59), leading to a change from phenylalanine (TTC) to valine (GTA) at the preprohormone level of UCN3 peptide. Both SNPs only form two haplo- 0.046 less inches of SFD compared to the CC and CA genotypes (TABLE 1), which approached the significance level (P=0.0982 for the GLM analysis and P=0.0522 for the QTDT test when the P values were uncorrected). These data indicate that increasing SFD with a promoter polymorphism does not necessarily result in an increase of muscle fat accumulation. However, it is very likely that increasing muscle fat deposition with the exon 2 polymorphisms would also stimulate high accumulation of SFD, and thus lead to an overall increase of whole body fat deposition. As muscle lipid accumulation in muscle is a major contributor to both insulin resistance and whole body fat deposition, inhibiting fat gain in muscle should be a long-term goal for preventing obesity in human.

In the human genome, UCN3 is placed at position 5.40 Mb on 10p15.1, where two independent studies suggested quantitative trait loci (QTL) for body mass index (BMI) in Pima Indians (Lindsay RS, Kobes S, Knowler WC, Bennett PH, Hanson RL (2001) Genome-wide linkage analysis assessing parent-of-origin effects in the inheritance of type 2 diabetes and BMI in Pima Indians. Diabetes 50: 2850-2857) and in Caucasians (Chagnon YC, Rice T, Perusse L, Borecki I B, Ho-Kim M A et al. (2001) Genomic scan for genes affecting body composition before and after training in Caucasians from HERITAGE. J Appl Physiol 90: 1777-1787). Interestingly, both groups used the same flanking markers— D10S1435 and D10S189, spanning from 2.23 Mb to 6.76 Mb on human chromosome 10. Obviously, the UCN3 gene should be a strong candidate gene for the human BMI QTL detected in the region as Applicants' current study provided strong evidence supporting its involvement in regulation of lipogenesis.

On the other hand, evidence has shown that UCN3 is directly involved in regulation of glucagons and insulin secretion (Li C, Chen P, Vaughan J, Blount A, Chen A et al. (2003) Urocortin III is expressed in pancreatic beta-cells and stimulates insulin and glucagon secretion. Endocrinology 144: 3216-3224). Injection of murine synthetic UcnIII into male rats significantly increased both blood and insulin levels. UCN3 also stimulated glucagons and insulin release from the isolated rat islets. In the present study, the high SFD associated haplotype CTAT in the promoter region gained 10 new transcriptional regulatory biding sites in comparison with the other haplotype of TCAT in the bovine UCN3 gene. Among these 10 transcriptional regulatory binding sites, three are for TFCP2 (transcription factor CP2), NKX3-1 (NK3 transcription factor related, locus 1) and NFAT5 (nuclear factor of activated T-cells 5, tonicity-responsive). Studies have shown that these three genes may affect the risk of Alzheimer's disease (Bertram L, Parkinson M, McQueen M B, Mullin K, Hsiao M et al. (2005) Further evidence for LBP-1c/CP2/LSF association in Alzheimer's disease families. J Med Genet 42: 857-862), prostate cancer (Gelmann E P, Steadman D J, Ma J, Ahronovitz N, Voeller H J et al. (2002) Occurrence of NKX3.1 C154T polymorphism in men with and without prostate cancer and studies of its effect on protein function. Cancer Res 62: 2654-2659) and diabetic nephropathy (Yang B, Hodgkinson A D, Oates P J, Kwon H M, Millward B A et al. (2006) Elevated activity of transcription factor nuclear factor of activated T-cells 5 (NFAT5) and diabetic nephropathy. Diabetes 55: 1450-14554), conditions often associated with obesity. All these data clearly support that the UCN3 gene play an important role in regulation of adipocyte metabolism through a broad pathway.

In conclusion, Applicants annotated the bovine UCN3 gene using a comparative approach and developed a total of 12 genetic markers in the gene. Genotyping these markers on ~250 Wagyu x Limousin $F_2$ crosses revealed that the bovine UCN3 gene is significantly associated with lipid accumulation in muscle and subcutaneous fat depth in cattle. The promoter polymorphisms of the bovine UCN3 gene alter 12 potential transcription regulatory binding sites, some of which are associated with obesity-related conditions. The coding polymorphisms of the gene affect the secondary structure of UCN3 mRNA remarkably. Therefore, according to particular aspects, Applicants disclosed UCN3 as a strong target for developing antiobesity drugs.

Example 2

Figure 5:
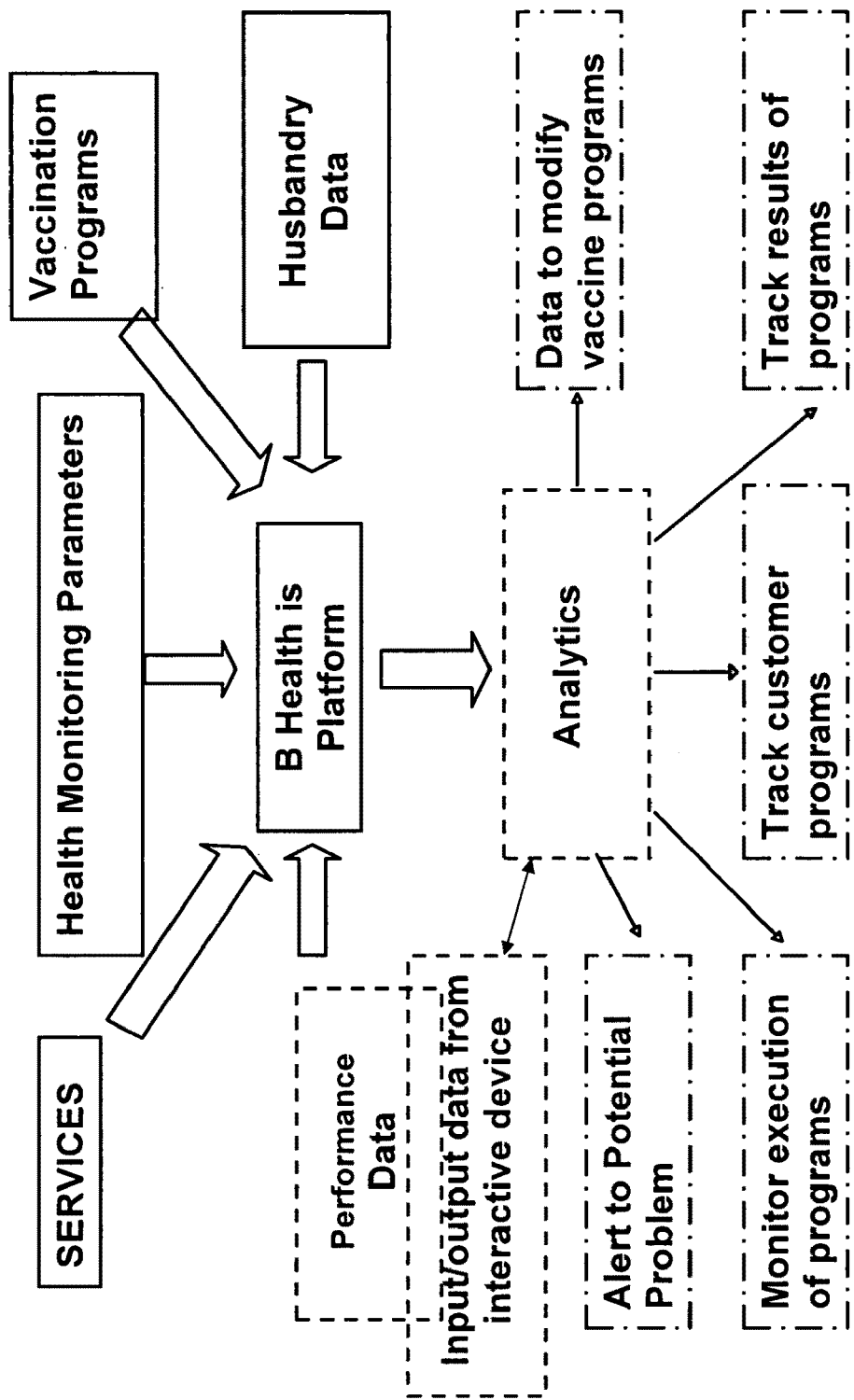
FIG. 5 illustrates a flowchart of the input of data and the output of results from the analysis and correlation of the data pertaining to the breeding, veterinarian histories and performance requirements of a group of animals such as from a herd of cows and the interactive flow of data from the computer-assisted device to a body of students learning the use of the method of the invention.

FIG. 5 shows a flowchart of the input of data and the output of results from the analysis and correlation of the data pertaining to the breeding, veterinarian histories and performance requirements of a group of animals such as from bovines. The flowchart further indicates the interactive flow of data from the computer-assisted device to a body of students learning the use of the method of the invention and the correlation of such interactive data to present an output as a pie-chart indicating the progress of the class. The flowchart further indicates modifications of the method of the invention in accordance with the information received from the students to advance the teaching process or optimize the method to satisfy the needs of the students.

Figure 6:
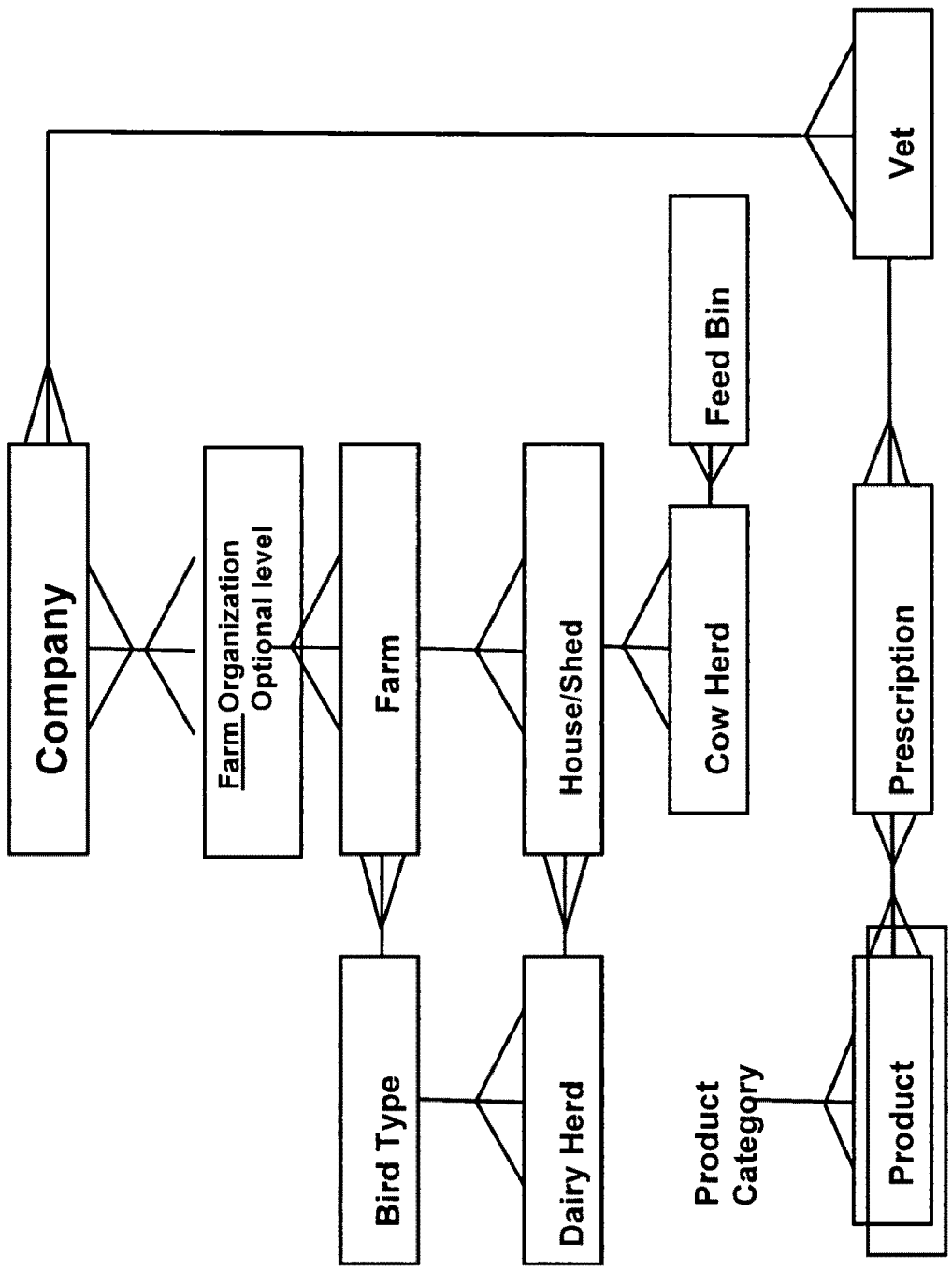
FIG. 6 illustrates potential relationships between the data elements to be entered into the system. Unidirectional arrows indicate, for example, that a barn is typically owned by only one farm, whereas a farm may own several barns. Similarly, a prescription may include veterinarian products.

FIG. 6 illustrates potential relationships between the data elements to be entered into the system. Unidirectional arrows indicate, for example, that a barn is typically owned by only one farm, whereas a farm may own several barns. Similarly, a prescription may include veterinarian products.

Figure 7A:
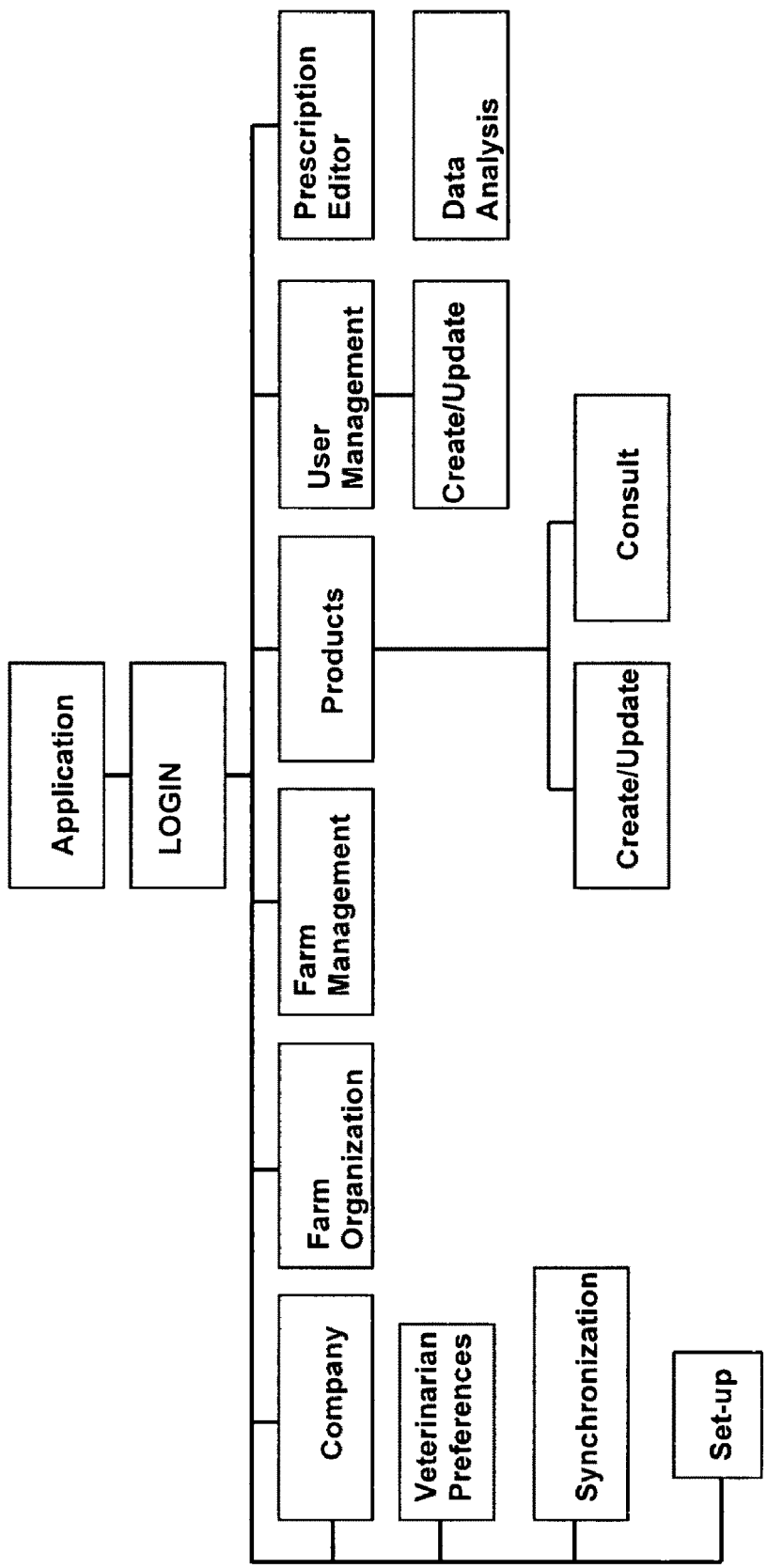
FIG. 7A illustrates the flow of events in the use of the portable computer-based system for data entry on the breeding and rearing of a herd of cows.
Figure 7B:
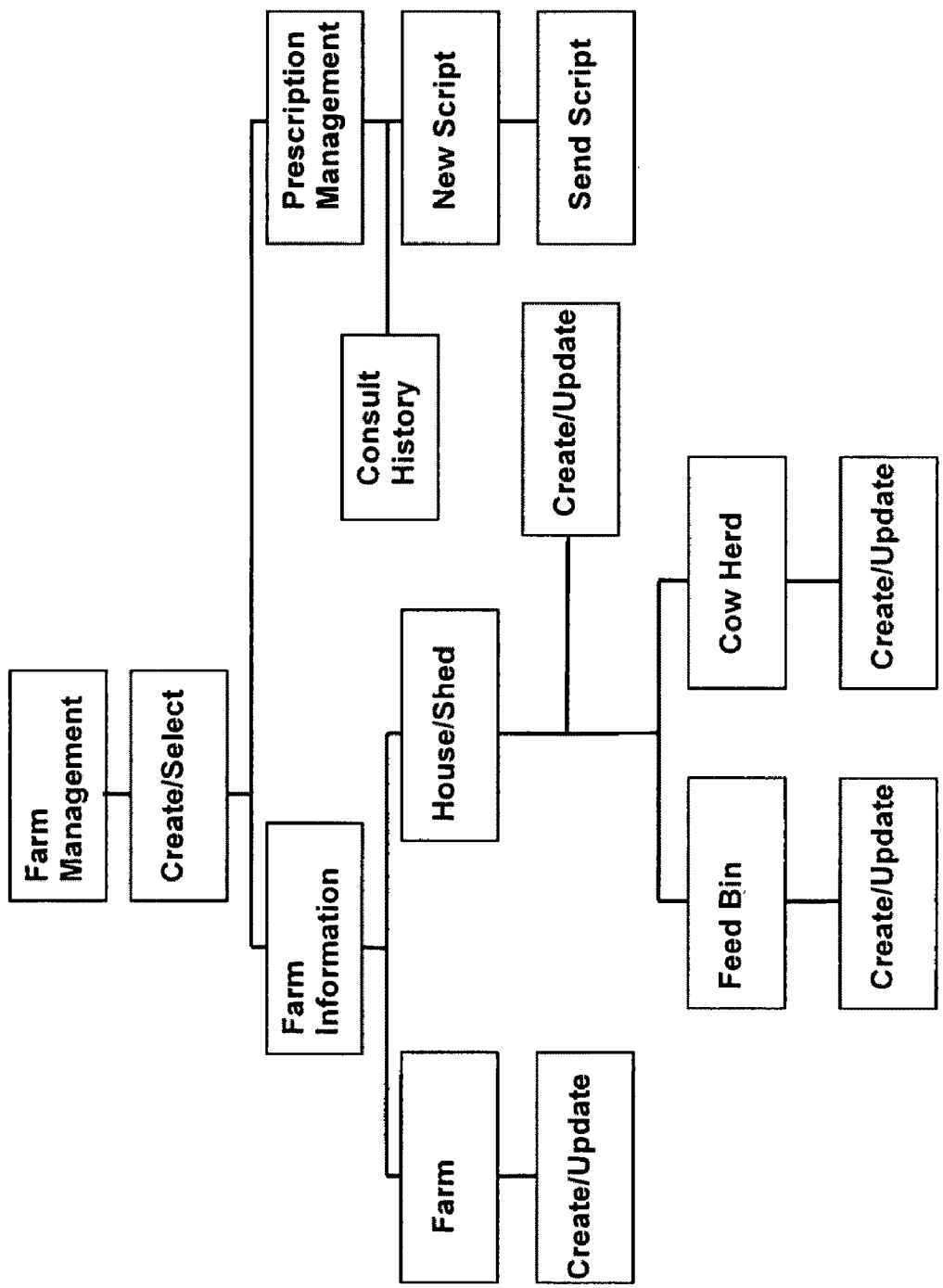
FIG. 7B illustrates the flow of events through the subroutines related to data entry concerning farm management.
Figure 7C:
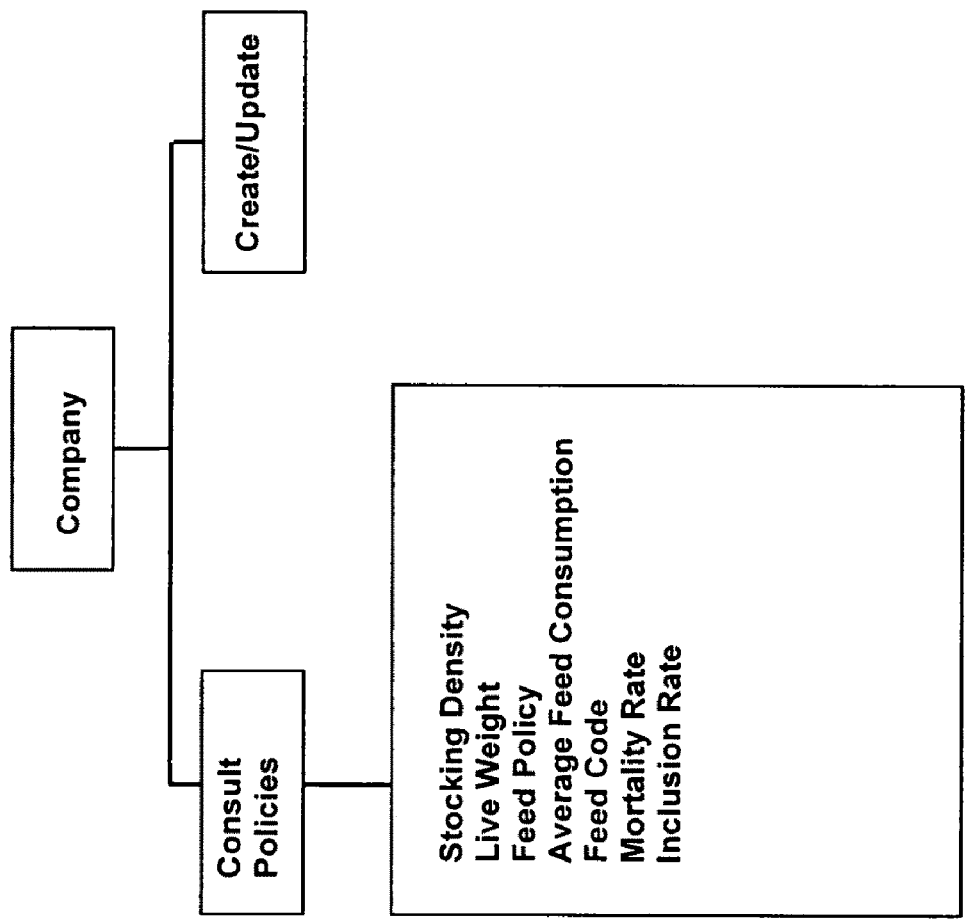
FIG. 7C illustrates the flow of events through the subroutines related to data entry concerning data specific to a company.

FIG. 7A illustrates the flow of events in the use of the portable computer-based system for data entry on the breeding and rearing of a herd of cows. FIG. 7B illustrates the flow of events through the sub-routines related to data entry concerning farm management. FIG. 7C illustrates the flow of events through the sub-routines related to data entry concerning data specific to a company.

Figure 8:
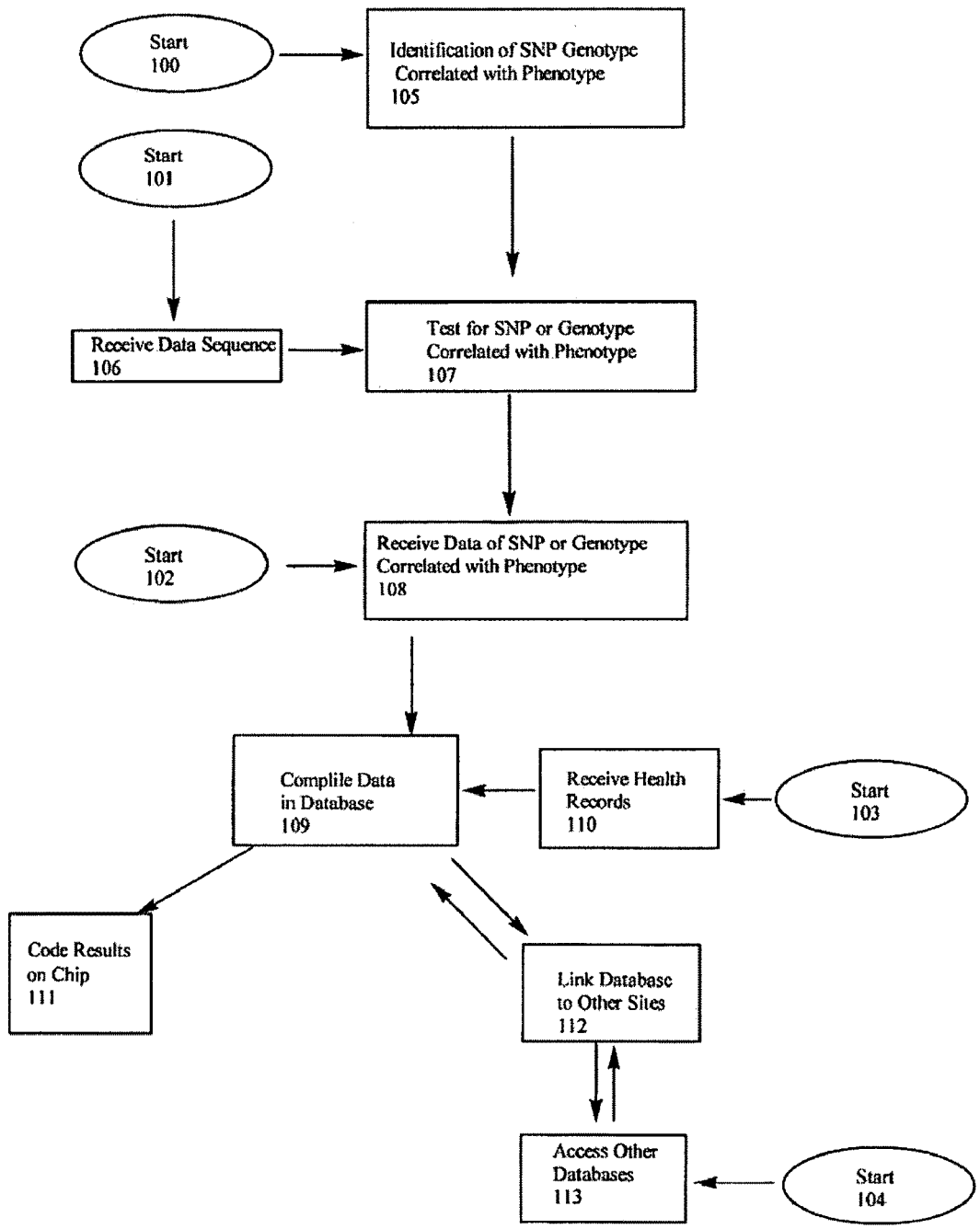
FIG. 8 illustrates a flow chart of the input of data and the output of results from the analysis and the correlation of the data pertaining to the breeding, veterinarian histories, and performance requirements of a group of animals.

FIG. 8 illustrates a flow chart of the input of data and the output of results from the analysis and the correlation of the data pertaining to the breeding, veterinarian histories, and performance requirements of a group of animals.

The invention is further described by the following numbered paragraphs:

1. A method for sub-grouping animals according to genotype wherein the animals of each sub-group have a similar polymorphism in a UCN3 gene comprising:

(a) determining the genotype of each animal to be sub-grouped by determining the presence of a single nucleotide polymorphism in the UCN3 gene, and (b) segregating individual animals into sub-groups wherein each animal in a sub-group has a similar polymorphism in the UCN3 gene.

2. A method for sub-grouping animals according to genotype wherein the animals of each sub-group have a similar genotype in the UCN3 gene comprising:

(a) determining the genotype of each animal to be sub-grouped by determining the presence of a single nucleotide polymorphism(s) of interest in the UCN3 gene, (b) segregating individual animals into sub-groups depending on whether the animals have, or do not have, the single nucleotide polymorphism(s) in the UCN3 gene.

3. The method of paragraphs 1 or 2, wherein the single nucleotide polymorphism(s) of interest selected from the group consisting of AAFC03043460.1:g.8272-8281AATAATAAAT(SEQ ID NO:9)>GGAGC, g.8208C>T, g.8265C>T, g.8287T>C, g.8412A>G, g.8426T>A, c.8786C>T, g.9074T>C, c.12609C>T, c.12621>C, c.12667T>G and c.12669C>A.

4. A method for sub-grouping animals according to genotype wherein the animals of each sub-group have a similar genotype in the UCN3 gene comprising:

(a) determining the genotype of each animal to be sub-grouped by determining the presence of a nucleotide polymorphism(s) of interest selected from the group consisting of AAFC03043460.1:g.8272-8281AATAATAAAT(SEQ ID NO:9)>GGAGC, g.8208C>T, g.8265C>T, g.8287T>C, g.8412A>G, g.8426TA, c.8786C>T, g.90747>C, c.12609C>T, c.12621T>C, c.12667T>G and c.12669C>A and (b) segregating individual animals into sub-groups depending on whether the animals have, or do not have, a nucleotide polymorphism(s) of interest selected from the group consisting of AAFC03043460.1:g.8272-8281AATAATAAAT(SEQ ID NO:9)>GGAGC, g.8208C>T, g.8265C>T, g.8287T>C, g.8412A>G, g.8426T>A, c.8786C>T, g.9074T>C, c.12609C>T, c.12621T>C, c.12667T>G and c.12669C>A.

5. A method for identifying an animal having a desirable phenotype as compared to the general population of animals of that species, comprising determining the presence of a nucleotide polymorphism in the UCN3 gene of the animal, wherein the polymorphism is selected from the group consisting of AAFC03043460.1:g.8272-8281AATAATAAAT (SEQ ID NO: 9)>GGAGC, g.8208C>T, g.8265C>T, g.8287T>C, g.8412A>G, g.8426T>A, c.8786C>T, g 9074T>C, c.12609C>T, c.12621T>C, c.12667T>G and c.12669C>A, wherein the single nucleotide polymorphism is indicative of a desirable phenotype.

6. The method of paragraph 5, wherein the desirable phenotype is intramuscular fat deposition.

7. The method of any one of paragraphs 1 to 6 wherein the animal is a bovine.

8. The method of any one of paragraphs 1 to 7 wherein the UCN3 gene is a bovine UCN3 gene.

9. An interactive computer-assisted method for tracking the rearing of livestock bovines comprising, using a computer system comprising a programmed computer comprising a processor, a data storage system, an input device, an output device, and an interactive device, the steps of: (a) inputting into the programmed computer through the input device data comprising a breeding history of a bovine or herd of bovines, (b) inputting into the programmed computer through the input device data comprising a veterinary history of a bovine or herd of bovines, (c) correlating the veterinary data with the breeding history of the bovine or herd of bovines using the processor and the data storage system, and (d) outputting to the output device the breeding history and the veterinary history of the bovine or herd of bovines.

10. The method according to paragraph 9, wherein the computer system is an interactive system whereby modifications to the output of the computer-assisted method may be correlated according to the input from the interactive device.

11. The method according to paragraph 9 or 10, further comprising the steps of inputting into the programmed computer diagnostic data related to the health of the cow or herd of cows; and correlating the diagnostic data to the breeding and veterinary histories of the cow or herd of cows.

12. The method according to any one of paragraphs 9 to 11, wherein the veterinary data comprises a vaccination record for a cow or herd of cows.

13. The method according to any one of paragraphs 9 to 12 wherein the health data is selected from the group consisting of husbandry condition data, herd history, and food safety data.

14. The method according to any one of paragraphs 9 to 13, further comprising at least one further step selected from the group consisting of inputting into the programmed computer data related to the quality control of the bovine or herd of bovines and correlating the quality control data to the breeding and veterinary histories of the cow or herd of cows, inputting into the programmed computer performance parameters of the cow or herd of cows; and correlating the required performance parameters of the bovine or herd of bovines to a specific performance requirement of a customer, correlating the vaccine data to the performance parameters of the bovine or herd of bovines, correlating herd to the performance parameters of the bovine or herd of bovines, correlating the food safety data to the performance parameters of the bovine or herd of bovines, correlating the husbandry condition data to the performance parameters of the bovine or herd of bovines, inputting into the programmed computer data related to the nutritional data of the bovine or herd of bovines; and correlating the nutritional data to the performance parameters of the bovine or herd of bovines, and alerting to undesirable changes in the performance parameters of the bovine or herd of bovines.

15. The method according to any one of paragraphs 9 to 14, further comprising the steps of inputting into the programmed computer through the input device data comprising a genotype of a bovine; correlating a physical characteristic predicted by the genotype using the processor and the data storage system; and outputting to the output device the physical characteristic correlated to the genotype for a bovine or population of bovines, and feeding the animal(s) a diet based upon the physical characteristic, thereby improving bovine production.

16. The computer-assisted method according to any one of paragraphs 9 to 15 for optimizing efficiency of feedlots for livestock comprising outputting to the output device the breeding and veterinary history of the bovine or herd of bovines and feeding the animal(s) a diet based upon their breeding and veterinary histories, thereby optimizing efficiency of feedlots for the bovine or herd of bovines.

17. A method of transmitting data comprising transmission of information from such methods according to any one of paragraphs 9 to 15, selected from the group consisting of telecommunication, telephone, video conference, mass communication, a presentation, a computer presentation, a POWERPOINT™ presentation, internet, email, and documentary communication.

18. An interactive computer system according to any one of paragraphs 9 to 15 for tracking breeding and welfare histories of cows comprising breeding and veterinarian data corresponding to a bovine or herd of bovines, and wherein the computer system is configured to allow the operator thereof to exchange data with the device or a remote database.

19. The interactive computer system according to paragraph 18, wherein the input and output devices are a personal digital assistant or a pocket computer.

20. A method of doing business for tracking breeding and welfare histories of livestock comprising breeding and veterinarian data corresponding to one or more livestock animals comprising providing to a user the computer system of paragraph 18.

21. A method of doing business for tracking breeding and welfare histories of livestock comprising breeding and veterinarian data corresponding to one or more livestock animals comprising providing to a user the computer system of paragraph 19.

22. The method of doing business according to paragraph 20, further comprising providing the animal owner or customer with sample collection equipment, such as swabs and tags useful for collecting samples from which genetic data may be obtained, and wherein the tags are optionally packaged in a container which is encoded with identifying indicia.

23. The method of doing business according any one of paragraphs 9 to 15, wherein the computer system further comprises a plurality of interactive devices and wherein the method further comprises the steps of a receiving data from the interactive devices, compiling the data, outputting the data to indicate the response of a student or class of students to a question relating to the operation of the computer-assisted method, and optionally modifying the operation of the computer-assisted method in accordance with the indication of the response.

24. The method of any one of paragraphs 9 to 24 wherein the data comprises presence or absence of one or more of a nucleotide polymorphism(s) of interest in the UCN3 gene.

25. The method of paragraph 24 wherein the nucleotide polymorphism(s) is selected from the group consisting of AAFC03043460.1:g.8272-8281AATAATAAAT(SEQ ID NO: 9)>GGAGC, g.8208C>T, g.8265C>T, g.8287T>C, g.8412A>G, g.8426T>A, c.8786C>T, g.9074T>C, c.12609C>T, c.12621T>C, c.12667T>G and c.12669C>A.

26. A method for the diagnosis or monitoring of intramuscular fat deposition in a subject, comprising: obtaining a biological sample from a subject; and determining, using a suitable assay, a presence or absence in the sample of one or more UCN3 MNPs or SNPs, as described herein.

27. The method of paragraph 26, wherein the subject is bovine.

28. A method for marker-assisted selection to improve intramuscular fat deposition, comprising screening, as part of a selection scheme, based on one or more UCN3 MNPs or SNPs, as described herein, to enhance selection for intramuscular fat deposition.

29. A method for the diagnosis or monitoring of marbling in a subject, comprising: obtaining a biological sample from a subject; and determining, using a suitable assay, a presence or absence in the sample of one or more UCN3 MNPs or SNPs, as described herein.

30. The method of paragraph 29, wherein the subject is bovine.

31. A method for marker-assisted selection to improve marbling, comprising screening, as part of a selection scheme, based on one or more UCN3 MNPs or SNPs, as described herein, to enhance selection for intramuscular fat deposition.

32. The method of paragraph 31, wherein selecting is to improve marbling.

33. A method for the diagnosis or monitoring of subcutaneous fat depth in a subject, comprising: obtaining a biological sample from a subject; and determining, using a suitable assay, a presence or absence in the sample of one or more UCN3 MNPs or SNPs, as described herein.

34. The method of paragraph 33, wherein the subject is bovine.

35. A method for marker-assisted selection to reduce subcutaneous fat depth, comprising screening, as part of a selection scheme, based on one or more UCN3 MNPs or SNPs, as described herein, to enhance selection for subcutaneous fat depth.

36. The method of paragraph 35, wherein selecting is to and reduce subcutaneous fat depth.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for identifying a bovine animal as having a reduced subcutaneous fat depth (SFD) phenotype as compared to the general population of bovine animals, said method comprising:
  (a) obtaining a biological sample from a bovine animal, said sample comprising nucleic acids from said bovine animal;
  (b) detecting in said nucleic acids the nucleotide content at the g.8208C>T polymorphic position in the urocortin 3 (UNC3) gene, wherein the g.8208C>T polymorphic position is either a C or a T at position 8208 of SEQ ID NO: 8; and
  (c) correlating the nucleotide content at the g.8208C>T polymorphic position in the urocortin 3 (UCN3) gene with the SFD phenotype of the bovine animal, wherein the presence of a C at position 8208 of SEQ ID NO: 8 is indicative of a greater SFD phenotype as compared to the general population of bovine animals.

* * * * *

```
                         SEQUENCE LISTING

<160> NUMBER OF SEQ ID NOS: 9

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggggctgcac caagcaaatg tcaac                                           25

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tctacccttc ttcctggagc caac                                            24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aggtctggga gagaaggtgg gtag                                            24

<210> SEQ ID NO 4
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 4
aaacacagac attgacggtt cagc                                          24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctgaacttgc acaaagcctg gtag                                          24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cccagcctcc tcctctactt cttc                                          24

<210> SEQ ID NO 7
<211> LENGTH: 908
<212> TYPE: DNA
<213> ORGANISM: Bos sp.

<400> SEQUENCE: 7
ctttgacaca aaaaaactgg aaaaaatgca ccaagcaaat gtcaaccaaa ggaaaactgg    60
aatagctgtt tcagtatcag acaaagcaga ctgtaagaca aaaagtgtta tttgatttga   120
aagggtttat agtcaaatta ttaaagggt tatttgcatt gagctggcca aaaagttcat    180
ttggaatgta gctaggctgt tcaataaagg tcttggtgaa aatgcaaact gtgcctaagc   240
ccacacactg cagctacyga gcccatgtac cgcaactgga gaaacctgca cactgcaatg   300
aagacccaga acagccaaaa taataataaa taagtgyttc cattgctcag tagctaagtc   360
gtgtctgact cttttttgac cccatggact gcagcacgcc aggcttccct gtccttcata   420
acctccagga gtttgctcaa acacttgtcc attgagttgg tratgccaaa gaaatwaaaa   480
aaaaaaaaaa aaaaactaat cacaggacag cagacaaact ttcttctcta ctttcaagca   540
ggtgttggct ccaggaagaa gggtagagag actgaaatta gtaagaacga agatgagtaa   600
taaaactctt caagaagct gcttctcagt ttaacagagt gtgttttttc ctttttatca    660
atgaagccag ttgctagggc aggaagggca gtgggggtg gggcggtga tgggaggtct    720 gggagagaag gtgggtagga gcggtcagag atgctgacag cttgtcatct ccgtgacgtg   780
cacagctgct tgggttgtat tttaaacggg atcacatccc agggtagaca ccgcgtctgg   840
atttatgatc caccccgtga tctgtcactt ttatgtatat gcacacacac gagggagtgg   900
agtggttt                                                           908

<210> SEQ ID NO 8
<211> LENGTH: 15359
<212> TYPE: DNA
```

<213> ORGANISM: Bos sp.

<400> SEQUENCE: 8

```
cttcatctga gatttagaga gagaaacgtt agagactgaa caagccagca acattcccca        60
gagaaatggt gaacttattt cccagtggag atagatgcgt cctgttcatc ctcacctctt       120
atactaagtg taaattttga tgtctgagtc ttttggtggc ccccaagatt ggacttggat       180
gtccttaatg taccctggtc tttccctctt atagtaatgg gtcatcccac tgtccagcca       240
cttccctctt tatccatctt cagcttactc cagcccacct ggcaggtgct tcagattcaa       300
gagaccttaa tttgcattct gatatattgc tattaagact gaaaactgct acttattgtt       360
atagaggaca attggcaata tttgtctaat cttatcatat cttttgggct tccctggtgg       420
ctttaaaaat tataaagaa cagtctttga tctggcagtt cttacacatt taaccaaaca       480
cttaatcttc caagtgaagg atgaacagga atgatcctct ctcaacagga atgagttca       540
tcatttgttc tgaaagatgc tgctttgaag gcaagaatca tgactatcct gctccatctt       600
caattttcag aagtcaagac tgtccctaac acccataggc attcaataaa tatttaagtg       660
aacaattgac cttaccaaaa attcaaattg ccttcatcat gtaaaaccta ttttataaa       720
ctcagtttgc tcctcttcca aacgggacag ttaactagtc ctattgtttt gaaagggcaa       780
aacagggtgt ctctgaagct cttcctgagt tgaaaactga acatttatt actgacattt        840
aagtgttgct cccacctact ccccctttgc aaatatttct gaagaaaatt catttccaga       900
tagatatatc ctcatttaca tctaattctc tgcatattac tcagtggagg agggccagca       960
aaggttaggg catcggagaa aggtgacaac cagagactcg agtgaatgca gagctttaat      1020
tggcaattag tcagaatgaa gtaagagatg gtggaactgg gtgcctgttc tagtacgcag      1080
caaagaactc tgcattgtga ccgcattaca aagaacacgg aagatatctt tccattttat      1140
ctaagtcaat gtacttaagg gcagagaggt gtttgtcaca gtcattactg tcctgaaggg      1200
tcaataatga agttcctctt ggattcctga tatcagtaat ttgggtcttc tctcttttat      1260
tcatggtcta gctagaggtt tataaattct gttgctcttc aaaaaatacc agcttttgtt      1320
ttcattgttc ctctcatttt ctagtctcta tttcatatat atatgtatat atacacaatg      1380
atgtatatca cactgcatgt gtgtatatat atatatatat atatctctac tctaagatat      1440
atatatatac tctgaagctg aaactccaat actttggcca cctgatgtga agaactgact      1500
cattggaaaa gaccctgatg ttggaaaaga ttgaaggcag gagaagggg tgacagagaa       1560
tgagagggtt ggatggcatc accaacttga tgaacatgag tttgagcaag gtccgggagt      1620
tggtgatgga cagggaagcc tggcgtgctg cagtccctgg ggtcacaaag agttggacat      1680
gatggagtga ctgaacggaa ctgactctta tctttactac ttaaattcct tgctttggac      1740
ttaactcgtt tttctttttc tacgtgaaag cttagatcac tggtttgaga cctctcttct      1800
cttcccatat aagcatttaa aactataaat ttcctctgta tgctgctttg aatacatgcc      1860
acaattctta atatattgaa ggagcaattc aaatttcaag gggtatgcaa gtcaagctgt      1920
gttcctcgaa gatttaaaaa gctgatcatt tcctcataca acaccccccca cacacacaca      1980
cacacataca caatcacaat gttgatattt ggttaattta gataaggagt atacctttgt      2040
tcatcacact catttctact ttcctggaaa ctttctgaaa aacaattgga gttttaaaag      2100
agtgcacaga aagttattgg ggcaactgcc ttgttttaca gggcttccca ggctaatgca      2160
ggagacatag gttcatccct gggtccagaa gatcctatgg aggaggaaat ggcaacccac      2220
tccggtattc ttgcctacaa aatttcaaga acagagaaga ctggcaggct acagtccata      2280
```

```
gtatcgcaaa gagtcagata cgactgagca caaatgcttg ttttacaaga gagacagtga   2340
gcttgcaatc atggtaaggc actaagaagc tgccatcttc aataacaagg tttggattgt   2400
tgaaaacaag cctaggagag aaggaccagc tggtgggaat gaacaatgga ctgtcatgag   2460
ggaggatctc attttcacct ctgagctgct gcagggagac tccagggtgt ggtgatgttt   2520
tcattagcag ctcaggttca gcccaggctt ctctaccttc acaccgcgt aacatcagtg   2580 ctatttcctg cagaccccag gacctcagca ggcacccgct gctcaccaag atgactgtgg   2640
agacatccct tcccacatgg gaacatgagc aatcctgaga gctgtccacc gtccagagtg   2700
tgacatgaag gaacagatgt catcagcccc aggacagaga gtaggtggaa agcaagtctg   2760
ggatgaacag agagaaatgc agattttaa atgttcacaa aggcagggag agaggaagaa   2820
agggtagaat ataaaataac acctacgcta tggctacaaa ttcatgcacc catgttttct   2880
cagattacca gttcagtttc tcatgccttg gtctgatgac gtgggacctg cagtccacac   2940
cgcctccaag gcccaacaag cgatttctgg gcctgtctta ctgaacaata cttttaattt   3000
catccacttt tggcccctca ccatggtaaa aaggtgtcct tcccaaagtt acaggccctg   3060
ggacctgtaa ctttccaaag ttataagccc tgggacctgt aacttcccaa agttacaggc   3120
catgggacca aagtgacact gggctttcac tggggagtaa agtcaagctg ggagaaggca   3180
atggcacccc actccagtat tcttgcctgg agaatcccag ggatggggaa gcctggtggg   3240
gtgccgtcta tggggtcgca cagagtcgga catgactgaa gcaacttagc agcaacagca   3300
gcaaagtcaa gctgtgttcc acagaggatt aaaaagctga tcatgtctgg gcttccccag   3360
tggctcagtg gtaaagaatc tgcctgccag tgcaggaaac ccaggtttga tttctggtcc   3420
aggaagatcc cacatagccc cctaggagcc actatgccca tgcaccacaa ctgctgtgtg   3480
ccctagagcc caggagccgc aactactgac cccacaacca caacagctga gctcctgcac   3540
ctggagctcg tgccctgaga cgcaccacaa cgcgaagccc acaccccaca actacagagg   3600
agcccccact cgccgcaact agaggaagag cctaagcggc aacaaagtcc caacacagcc   3660
aaaaataaat agaattattt taaaaacaaa ttaaagctt atcatttcca atcttcttgt   3720
gaggctctct tcccatttaa ctacctgatt cttcaaactt gtctacaaaa atactcctgt   3780
gatacagcct ttggttagcg cttccaaagg ctgttcttct cacctgaggc tcttattaaa   3840
aggaagtttg attcattagg gctgaggtga gattctgcat ctctaaaagc tcccagggat   3900
gctgaggttg aaggtccatg gaccacagtt tgagcagctg gcttctatag ttcttagtac   3960
ttactatagt ccttagtatt aaatattaac cacttgtgtt tcttgtcctt agtaggtcta   4020
caataaacct gacttggagg gatggctttt tgattgaagt atagttgatt tacaatgctg   4080
tcttagattc tgatgctgct gttgttgttg ttcagtcact aagtcgtgtt caactcttgg   4140
tgacctatgg actgctgctc accaggctcc tctgtcctcc actacctccc ggagtttgct   4200
caaattcatg tcgatgatgc tatcccaacc atctcatcct cttccacccc ctactccttt   4260
tgccttcaat ctttcccaga atcaagatct tttccaatga gttgactctt cacaccaggg   4320
ggccaaagta ttagagcttt tagtttctgc tgtacagcaa agtgaatcag ctatatgtat   4380
acatataccc ctcttttttg gatttccttc ccatttaggt caccacaggg cattgaggaa   4440
agttccctgt gctatacagc aggttctcat tggttatctg ttttatacac agtatcaata   4500
gtgaatatat gtcaatccca atctcctaat tcatcccatg gagctatgat tgaatttatt   4560 aaatgttct acagtagtag aataaagagg gaaagcttta ccaacacatc agtctttcat   4620
```

```
cctactcatg ttccctctct tttcttggag ttaaggaagc cagggcataa ttgggtggag    4680
gcagacttgg caaagtggtg tttctttct ggcttataga gcaaaacaag aaaggctgga     4740
ggtggagtca gtggtggagg tctctgccca tgtggccagt gatccagcac catgggatga   4800
acctgctttt cctgtttgta gcagctctcc tccctaacct catgacaatt actggccaaa   4860
attcagaact gtctgttttt tactctcccc ctactatttc tgtcttgtac acctgtatac   4920
aaacaagtgt actccctgaa atttgaattg ttccttctgc ctctacaatg gaaactgtag   4980
gattttatac tctaaaaagc caactatagt gatgacatca ctgtcttcta acccagcctc   5040
attctgtgga gacctgcaca catatccttc accctccctt gattattaga gatgaaatgg   5100
aatctcaatg caatttgagt ccccgtaact tgtcttttg aataaacctc taataatctc    5160
tttttaattt catttcaata ctattatctt caattatggg ctccgtgtct acaacaatcc   5220
ctcactctca aggccaagtt ctgttctctc cttgtagttg gaaatgcagg cttatccagc   5280
tttgcaaaag atcatcct tgagaatgtt catgtcgggg gcctgagttc tgaggttcac     5340
ctgtgtgtga ccccagctaa gagactgaac tagagcatga actctctttt aggccaaaca   5400
ttctgtgatt ctgtaagagt tcatgcaaac aaaagcattt aaaatactaa agaatgtctg   5460
ttgggacttc cctgctggtc cagtggctaa gactccacgc tcccaatgca gggggcccag   5520
gttctatccc tggtcaggga actagatccc acatgccaca gctaagactc aatgcagcta   5580
aataaatttt ttttaatata tattatctgt ttggatatat gtgacgggtt gcaattgtat   5640
atgcacatat acggagctac tgaataagga ggatcaacct cacttgttga gtctctgcta   5700
aacagcagat gctgtgttca tggtgctttt cctggcatag acttcagtct caagctgctt   5760
acagacaaac ggacacagtc aggagaagac cacagccagt ctcaaagcct agacttgcca   5820
agggaaacag attaaaattc acagtagata ggaacatggt ggtttatttc tgattgattg   5880
attgattggt gaactgatta agcatagtcc ctgattagct ggcaggcata ctttggccac   5940
atgatgcgaa gagttgactc attagaaaag accccaatgc aagaaagatt gaaggcagga   6000
ggagaagggg atgacagagc atgaccaact cgatggacat gagtttgagc aagcttcagg   6060
agctggtgat ggacagggaa gcctggtgtg ctgcagtcca tggggtcgca aagagtcaga   6120
catgactgaa ctgaactgaa taataacata gtgtgctatg tgttgggctt cccctcgatg   6180
gctcagcagt aaagtatctg ccagcaatgc aggagatgta agagatgtgg gttcaatccc   6240
tgggtcagga aaagctcctg gaggaggcca tggcaactca ctccagtatt cctgcctgga   6300
aaagtccatg gacagagaag cctggtgggc tacagtccac agggctgcaa agagtgggac   6360
atgaccgagc aactgaacaa catatagata agagattctg aaacatgttc aggggtgggg   6420
gtggcagagt gcgtgtatta gccttggaag aacgtgggct gcttggttac cattactact   6480
tacttttccc atgagcagaa ccacaagtga gctcaccatc ctggccccat ctgggagcat   6540
gctgcccagt ccactgcttt gtaagatgtt cggaagagtt tccaattccc ttgtcaatag   6600
agaaaacatg tcccctaagt gtatctgttg gtgttgatcc ccttgtctac aggtcaggta   6660
aacagggcac tgtgattgtg tccacatgtg gaaagtggc tatggggcag tttgcaagtt    6720
tgcccaagaa gccaacgtcc tccccttccc ctggaaggag acagaaagct tttttttttt   6780
ttaaggttat tactttacta tttatttatt tggccatgca acatgaggga tcttagttca   6840
ctgaccaggg atcaaaccca caccccctgc aagggcagca tggagtctta accactggac   6900
catcaaggaa gtaagtccca gacagaaagc tctgatgctg tttcacgagg ccccgaggga   6960
ggcagctgcc tctagcctgt ggctcccagg agctttgctc caggaatcaa tcagccacta   7020
```

```
aaagtccatc agagaggatc ataaaacgtc tgtaattcac catggcacct ggacacagag    7080
acaggctgga actgtcccca cctgtttcca ccgctgctgg tttcaggggg gatgcaaagt    7140
ccaatgagat tgattcctga taggtggata ggagacagcg ctagagaacc catatcagaa    7200
aggactggat gttaatgcag gatcatgggt gtgctgttat tatagaagta cagttactaa    7260
taactaaatc agtcctgcct gttgggaaaa acaagagtca aggcaagggt ctccccttac    7320
ttcacagacc agagaaattt caccaggtta caggggctc tgttcatgtg tgaggtgtag    7380
tgaatcagtg ctcagagcaa gaactgtagt ttttgcatgc tcatttgctc agtggtgtcc    7440
gacactgtgt gaccccatgg actgtagccc accagactcc tctgtccttg ggattctcca    7500
ggcaagaata ctggagaggg ctgccatttc ctcctccagg ggatattccc aacccaggaa    7560
tcaaaccaga gtctcttaca gctcctgcat tggcaagatg gttctttacc actgagccac    7620
cagggaagcc ccaattgtag ttttaaatgc ctagatacaa actaatagcg gggaaaatga    7680
aatgaaaatt taatcaatct agaagaacac agacaaggaa aaagagaaat aaacagaaac    7740
agaggggggaa agcagaccaa ataggaaatg ttttacatgt gaaacagcag aaaataatcc    7800
gaaaacatca gtaatcatta ttcatacaaa tgtgtcacgt cagtgatcac tattagtaca    7860
aactaataca aaggcctgta ttaaggcctt gttaatacag agatggttga ttagattttt    7920
taatttcagt atatacccctt cacaaaagaa ctttgacaca aaaaaactgg aaaaaatgca    7980
ccaagcaaat gtcaaccaaa ggaaaactgg aatagctgtt tcagtatcag acaaagcaga    8040
ctgtaagaca aaaagtgtta tttgatttga aagggtttat agtcaaatta ttaaaggggt    8100
tatttgcatt gagctggcca aaaagttcat ttggaatgta gctaggctgt tcaataaagg    8160
tcttggtgaa aatgcaaact gtgcctaagc ccacacactg cagctaccga gcccatgtac    8220
cgcaactgga gaaacctgca cactgcaatg aagacccaga acagccaaaa taataataaa    8280
taagtgtttc cattgctcag tagctaagtc gtgtctgact cttttttgac cccatggact    8340
gcagcacgcc aggcttccct gtccttcata acctccagga gtttgctcaa acacttgtcc    8400
attgagttgg taatgccaaa gaaattaaaa aaaaaaaaa aaaaactaat cacaggacag    8460
cagacaaact ttcttctcta ctttcaagca ggtgttggct ccaggaagaa gggtagagag    8520
actgaaatta gtaagaacga agatgagtaa taaaactctt caaagaagct gcttctcagt    8580
ttaacagagt gtgttttttc ctttttatca atgaagccag ttgctagggc aggaagggca    8640
gtgggggtg gggcggtga tgggaggtct gggagagaag gtgggtagga gcggtcagag    8700
atgctgacag cttgtcatct ccgtgacgtg cacagctgct tgggttgtat tttaaacggg    8760
atcacatccc agggtagaca ccgtgtctgg atttatgatc caccccgtga tctgtcactt    8820
ttatgtatat gcacacacac gagggagtgg agtggtttcc atagagagga aagatcacgg    8880
cccacttaca aacggcccac ttacaaacaa ttcaagaaaa ggagccggcg acccagaga    8940
agacagaagt tcgggggggga tgttcctggg gcagacctct cggttctgaa gctgcccgcc    9000
cgcctcactg agcatttgca ctccagagtg aagtctgctc acaggtaagg ctctggttgg    9060
ggacttccct atgaaggatc acttgatttg cccttaatta tgcaggaggt gctggggact    9120
ggatggggtg agcgataaga gttgcaagca cccctggggg cactgtgctg aaccgtcaat    9180
gtctgtgttt taaatgggga gaaggcagac ccaaagggac caagggggaag tttctcaggg    9240
ggggcaagag catcctcccc ccattagtag agaggcctgc tttgcaaaag gtaatagacc    9300
ggaagcagga tgggttctca caaacgtgtt tttctgaaca gagtccagtt gtgaacatga    9360
```

```
aaatcgtgtt tccagatggg gtggatgggg aagatggggg tggaaaccgg ggtaccagtc    9420
cctgctgcct gaccgatcgg gaaaatgctt gcatttcctg gttgctaagg catctccttt    9480
cgttctcttc atacacctgt gaggcaggta acgcctgctt tttaagatgc ggtgactgag    9540
aggttaagtg actgatggaa ggcatttgag ggtgagggag gttcgcagcc caggtcctct    9600
gccctcacag cctggagtcc tttcccsctg gccaccaggg acactggagg aagggaacag    9660
atgtctgtaa caattaggtg ccccccttg aaggggagag gccataaaga tggatgtttg    9720
atgtctccat ttgatgtcca agtgttctga gaaatcctgt ctgcagggtt ctcctgtaac    9780
acagcaatct agccagcatt cccacttctg aggatgaatg gagtcagaaa agcaacacaa    9840
aagcttccag taacaagtgt tatctagatc ttgtcaactt tctcctggct tttctccctc    9900
ttgggggaa aggcctttca tgaatgaacc ccctctgctc gctcaagtgt gaattgctaa    9960
gaagtgtgtg tgttacacat aaatgcttcc atgagtctgc agctcattac tataatatct   10020
ttcaaaatgc ttaaagggtc cctggggttca gcagtgactg tttataaag tgttttttta   10080
attcaacttc ttacccgtga ttgcagactg cgaactatct ctgccttcct agatgctgga   10140
aaatggggct gcctctgggc aaagcccgtg gtgtcctgca tttgcctcta gcttcacttt   10200
tttccttcag ggagctgtct ctcacaggtg ctctgaattt cagaccagct gagtccctcg   10260
ctgcctgtca ttctgggcac gacgtgactg tcacagctct tagaagcaag tgtccgtctc   10320
cagagaagca ctgccctaat aaccccaaa gaatggctga gtgtcaggta cccaaatgag   10380
aaaaatgaag atgaagaacg tttccctgta aacctaacta gatgggggcc acgtgttttc   10440
agagcaggta gcagggaaat cttaaacctt tgtactcttg cactatggta aaggcaaagg   10500
aatccaaaga atgtaagagg agaaacttgc ttaggaatca gacctgagta aggaggaaag   10560
gacgtttctt ttcttttgaca gtcctctctg ttcctgggat tggctccagg accgtcacag   10620
atccccagat gctcaagtcc cttatataaa ataatgtatt atttgcacat aatctacaaa   10680
catcctccca tgcaggggtg agtgctaagt cgcttcagtc gtgtccaatc ctttgcaacc   10740
ctatggacta tagcccgcca ggctcctctg tccatgggat tctccaggca tgaatactgg   10800
agtgggttgc catgtccttc tccaggagat cttccccgtc ttagggattg aacctgtgtc   10860
tcctgtattg gcaggcagat tctttaccac tagtgccacc tggaaagccc cacaatctcc   10920
catggtttta tgcaaatgct aaacaaagct aaactggaga gagagggaga aaggagaga   10980
gagaggagag cctggagctc aatccctaa tctcacagat gggaacacag ggaccagggg   11040
catttagtca ctgagccagt tagtgggagg tagggccgag cctgaccccct gaaaagagca   11100
ggggaccaag ggagagagag atagcgacag aaagagacag atcccctccc accccgaccc   11160
ccaccccgtt attaaccctt tctctgtgta ttggttttg gtttttttaa tctttttcagg   11220
cttatcaggc cctttgagag tgctcccaag ctttaaatg ccttcaaggc ataaggcagc   11280
taaagccaca attcatggat gtttatgcaa acaactaag gacagcctca atgaatgagg   11340
aaaccagaag tctgggtatt gagcacaata tcaaagaaa ggataagtcc attcttccac   11400
agtctaaaga gccctgtaaa atgttctccg ggaatcgggc acacagttct aaggacctcg   11460
gagatggata ggaacgctga gaaagtggtt cacaaagcgt ggtccatgaa cccacagcat   11520
cagcatcctc tagggatgtg ttagggatgc agattctcag gccttgcccc aaatctactg   11580
attcagaaat gctggagatg gggcccagca gctggtgttt gaacagttca ttcacgtgat   11640
tctgaacact ctgaagcgtg agaactgctg acttagagtt caaggcacga tgagcctacc   11700
tgggtaagag tggagcaaac agacgaaaaa agaaaagcca gaaaagcaac acaacaaaga   11760
```

```
taatggtctg caggatgaag ttccctggca tactatacat ctatatttat attcgtatga    11820
attatattca ttagttatat aatgtatagt acatttacag atacacagat acagatagat    11880
cacttctgag atggttgcct gtgtactgaa tcttatccta atagcacgtg gggattatta    11940
catgtaaaca gtcagtaacc aacacgcttc gttaagtatt tggttagaca gggagctttt    12000
ccactttaat ttaacctta cgagttagta cctattatcc cccattatta ttattatcat     12060
tattattatc agatgaggaa attgatgttc tcagaggtta agtaatctgc ctgccaccct    12120
caagcaaaca aggacccagt tggaatttga acctacctct gtctaactcc agagcctgtg    12180
tttcttttcca tgtgctaggt agctagttcc tacatctgga ccattcctac atctggcaac    12240
agtctgtcat catcaggctt gttaacacgc agattgctgg ccccagagct cttgactgac    12300
cagctctgga gcaagacccg agaatctctg cattgctaac aaatgtccat gatacacggc    12360
ctgcaagtcc agagaacacg ctttcaaaac ccggcaaagc tgaacttgca caaagcctgg    12420
tagatctgcc ccttctcccc ctgaaccta agaccctctc acacatatcg tcttttccg     12480
ctgcagggag agatgctcgt gccggccccc ttcctgctgg tcttgctact gctcctcggg    12540
gccccccagg tgggcctctc ccagaggtcc cccaaagccg gtccagccc cagctgcctc    12600
cacacagccc tacgtgaggc tgagaagagc cagcggaagg acacgtcgct gctgatcaag    12660
cggaccttcc ctgccctgcc ccgcggagac ccggaggacc aggaggggca ggaggaggag    12720
gacacagaga aaaggacctt ccctggctcc gtgggcggcg gcggtggcgg cggggccggc    12780
agcacccggt acaagtaccc atcccaggca cagttccagg ggcggccgtc ccaggacaag    12840
gccaatagtg accggcgcac caaggtcact ctgtccctgg acgtccccac taacattatg    12900
aacatcctct tcaacatcgc caaggccaag aacctgcgag ccaaggccgc cgccaacgcc    12960
cacctcatgg cccagattgg gcggaagaag tagaggagga ggctggggac ccctaggac    13020
gaggacggag gttgggggt ggacaggag ggttggcccg tcctgccagt ttctatcgga      13080
gggatcggcc ctggtttcca ggctctccac ccctctgtgc cttcccgcct ccagctgggc    13140
ccccacccct ctatatctac acacaccagc ggcctgttgt cccagatcca cagatggagg    13200
ccaccgtact gagacactga gatctaccct aggcgtctcc tttctccctc cccacaagga    13260
gaggcaaagg tcaggcaccc ctgccctcca ctccgctctc tgaccccaag aagaggggta    13320
cagggaggcc ctcccctccc cacaccaacc ccagcccagg caggaaggcg agggcgctga    13380
gcaccctgcc cccagaccct cattaaaacc cctctcaccc acattaaaac ccatggcttc    13440
ttgaacccct gactggtttc aattcctctt ccttcagtca gctgccttca ggcctccaag    13500
cttggaaagg ggcagctagt gagacagggt acaggtgagt ccgttcctga ccctcccagg    13560
acagtccctg gaggtcttgg gaggcatcaa gagcttggga aaggccaagc tggcaggacc    13620
ctgttggcta tcactggatc tgaagctggc tatgtggcca ggtccacca gaggcatagc     13680
cttgggtctg ctacagagtg ggccctggg tagaacgaaa gacaccccca gctcctccct    13740
ggcttgctag ggcctgagcc actaagtctg tcataggtgc ttcttgaatc gatggtcatt    13800
gtccagccca gtgctgggcc tagttaggga tactgacgtg ggaggcgcca aggcccttgc    13860
tatccatgag tcaacagtct taagtgaaca gacaaaaaca aaatgtgaaa gaagcaatt     13920
tcactaggga gtatataagt gatgaactgc aaggtcatag caattagtgt aaaaaataca    13980
aggaaatcag agcaagatga gaaggcttaa tatgagaagc agttcactaa aaatggacat    14040
cagcaagcac cctgatggcc tctggcagca gagctttctg catggtgaca agtcatgaat    14100
```

-continued

```
acatacaaag aacatcttca cgtgaaataa acctcatatg cacacaccac caccatcaga    14160
caaagtcaag agacaaacag acaacaaatt tggaaaaatg tttgccacac aggcaaaaga    14220
caagtatctt actgatcaaa tacgtaaaga gctaataact tcccaggtga cactactggt    14280
aaagaacctg cctgccattg caggagacat tcgatccctg ggttgggaag atcccctgga    14340
ggagggcatg gcaacccact ccagtgttct tgcctggaga atcccatgga gagaggagcc    14400
tggcgggcta cagtccatag ggttgcaaag agtcggacat gactggagca acttaacaca    14460
cacaaacacg cacacaaaat aactgaaaaa aaaaaacaat cgccctcaaa aaaataagca    14520
ggaatacata tatcacacac acacaaatac aagtgaccct taaatgtaca aacagatgct    14580
aaacttcact gctaaaaaaa gcacaactgc actcttacag aatttgtcac acatcagact    14640
ggcaaaatct gtttgacaat cggttcacac tgtgactgac aggtgcaaag cctccttcct    14700
tcactgatgg ttggtgggaa catgaattct gagaggcaat ctggaaaatc cgtatcaaaa    14760
ccacaaattc actttacctt taactcaaca accctgattc tggtgaacat tatttgaaaa    14820
ggcaaaactg tgcagttttt taaatgttaa gctaacttgg aaatgaaaaa tacccatct    14880 ctaaacagaa ccaatgctca aaaagctgaa atgcagctgt tttttccatc ctgggtgggg    14940
ggaaaaaacc ctcatgacac agcagaaata cctatgtgag tccgggttcc tcctcttctg    15000
tgtctctgag caaatccttt aacttccctc agcgttggtg tgccaggaac cctctttagg    15060
aacgagacgt cacggagttc tcacaagtat atttaacatt tattttttgtt ctaacagtgc    15120 gtgcagcatt ctgctcacac caaagatgca aaggacagga aattggcggg ggggtggggg    15180
ggggtgggaa ttagcttggt taaagaaaac tcaagcaggt atgacatttc cctgaacaac    15240
caaaaacact agaagaactt ccaagttggg gaaatggtac ctgcaagcac acccaagttc    15300
acagctatct cctcttaggg cctttggcta ggtgaacaaa gccttgaaga cagcagcct    15359
```

<210> SEQ ID NO 9
<211> LENGTH: 10
<212> TYPE: DNA
<213> ORGANISM: Bos sp.

<400> SEQUENCE: 9
aataataaat                                                          10